(12) United States Patent
Zhu et al.

(10) Patent No.: US 10,786,521 B2
(45) Date of Patent: *Sep. 29, 2020

(54) METHODS AND COMPOSITIONS FOR TREATMENT OF COPD DISEASES

(71) Applicant: Shanghai KE Pharmaceutical Co., LTD, Shanghai (CN)

(72) Inventors: Minsheng Zhu, Nanjing (CN); Jie Sun, Nanjing (CN); Yang Pan, Nanjing (CN)

(73) Assignee: SHANGHAI KE PHARMACEUTICAL CO., LTD (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,858

(22) Filed: Jul. 6, 2018

(65) Prior Publication Data

US 2018/0311265 A1 Nov. 1, 2018

Related U.S. Application Data

(63) Continuation of application No. 15/129,965, filed as application No. PCT/CN2015/076120 on Apr. 9, 2015, now Pat. No. 10,046,004.

(60) Provisional application No. 61/979,149, filed on Apr. 14, 2014.

(51) Int. Cl.

| | |
|---|---|
| A61K 31/704 | (2006.01) |
| A61P 11/06 | (2006.01) |
| C07H 15/256 | (2006.01) |
| A61K 31/7034 | (2006.01) |
| C07J 63/00 | (2006.01) |
| C07J 71/00 | (2006.01) |
| A61K 9/00 | (2006.01) |
| A61K 36/185 | (2006.01) |

(52) U.S. Cl.
CPC .......... *A61K 31/704* (2013.01); *A61K 9/0073* (2013.01); *A61K 31/7034* (2013.01); *A61K 36/185* (2013.01); *A61P 11/06* (2018.01); *C07H 15/256* (2013.01); *C07J 63/008* (2013.01); *C07J 71/0005* (2013.01)

(58) Field of Classification Search
None
See application file for complete search history.

(56) References Cited

U.S. PATENT DOCUMENTS

| | | | |
|---|---|---|---|
| 10,046,004 B2 * | 8/2018 | Zhu | ........................ C07J 63/008 |
| 2009/0285915 A1 | 11/2009 | Shan | |
| 2017/0173057 A1 | 6/2017 | Zhu et al. | |

FOREIGN PATENT DOCUMENTS

| | | |
|---|---|---|
| CN | 1298739 | 6/2001 |
| CN | 101274953 | 10/2008 |
| CN | 102499925 | 6/2012 |
| JP | 2006008597 A | 1/2006 |

OTHER PUBLICATIONS

Zhang et al., "Structure-Activity Relationship of Triterpenes and Triterpenoid Glycosides against Tobacco Mosaic Virus" Planta Medica vol. 73 pp. 1457-1463 (Year: 2007).*
Siegrist et al., "beta-Aminobutyric acid-mediated enhancement of resistance in tobacco to tobacco mosaic virus depends on the accumulation of salicylic acid" Physiological and Molecular Plant Pathology vol. 56 pp. 95-106 (Year: 2000).*
Aquino et al., "Saponins from the roots of Zygophyllum gaetulum and their effects on electrically-stimulated guinea-pig ileum" Phytochemistry 2001 vol. 56 pp. 393-398.
Li Li; Yong Peng; Guizhi Ma; Congfen He; Yuxiong Feng; Qifang Lei and Peigen Xiao "Quantitative Analysis of Five Kudinosides in the Large-leaved Kudingcha and Related Species from the Genus Ilex by UPLC-ELSO", Phytochemical Analysis, vol. 23, No. 6, May 17, 2012 (May 17, 2012).
Liu et al., Solid-phase extraction of ursolic acid from herb using p-cyclodextrin-based molecularly imprinted microspheres, J Sep Sci 2008. 31, 3573-3580.
Rang Jian-min; Xu Shi-Bo; Kong Yun-cheung "The effect of Kudingcha (Ilex Iatifolia Thunb.) on the contraction of Isolated guinea-pig tracheal smooth muscle in vitro", Zhongguo Zhongyao Zazhi, vol. 26, No. 12, Dec. 2001(Dec. 2001).
Seung-Hyung Kim; Jung-Hee Hong; Young-Cheol Lee, "Ursolic acid, a potential PPARy agonist, suppresses ovalbumin-induced airway inflammation and Penh by down-regulating IL-5, IL-13, and IL-17 in a mouse model of allergic asthma", European Journal of Pharmacology, vol. 701, No. 1, Nov. 28, 2012 (Nov. 28, 2012).
Tang et al., "Triterpene Saponins from the Leaves of Ilex kudingcha" Journal of Natural Products (2005) vol. 68 pp. 1169-1174.
Yu-Li Chen et al. Ilex kaushue and Its Bioactive Component 3,5-Dicaffeoylquinic Acid Protected Mice from Lipopolysaccharide-Induced Acute Lung Injury. Scientific Reports, vol. 6, No. 1, Sep. 29, 2016 (Sep. 29, 2016).
International Search Report issued in PCT/CN2015/076120 dated Sep. 6, 2015.
Written Opinion issued in PCT/CN2015/076120 dated Jul. 29, 2015.
International Preliminary Report on Patentability issued in PCT/CN2015/076120 dated Oct. 18, 2016.
Kim et al., "Ursolic acid, a potential PPARy agonist, suppresses ovalbumin-inducted airway inflammation and Penh by down-regulating IL-5, IL-13, and IL-17 in a mouse model of allergic asthma", European Journal of Pharmacology 701 (2013) 131-143.
Wu et al., "Effect of Satragaloside IV on the Increase of Microvascular Permeability Induced by Histamine in Pial Microvessels of Rat", China Journal of Chinese Materia Medica, vol. 26, No. 12, Dec. 2001. (with English Abstract).

* cited by examiner

*Primary Examiner* — Eric Olson
(74) *Attorney, Agent, or Firm* — Adsero IP

(57) ABSTRACT

The present disclosure relates to treatment of a pulmonary disease. The methods and kits provided herein facilitate relieving the symptoms resulting from the pulmonary disease (e.g., asthma, chronic obstructive pulmonary disease (COPD), etc.).

14 Claims, 16 Drawing Sheets

|  | $R_1$ | $R_2$ |
|---|---|---|
| Kudinoside G | Ara—³—Glc, 2-Rha | Glc |
| Kudinoside H | Ara | Glc |
| Ilekudinoside B | Glc A | Glc |
| Ilekudinoside E | Ara—³—Glc | Glc |

|  | $R_1$ | $R_2$ |
|---|---|---|
| Ilekudinoside C | Ara | Glc |

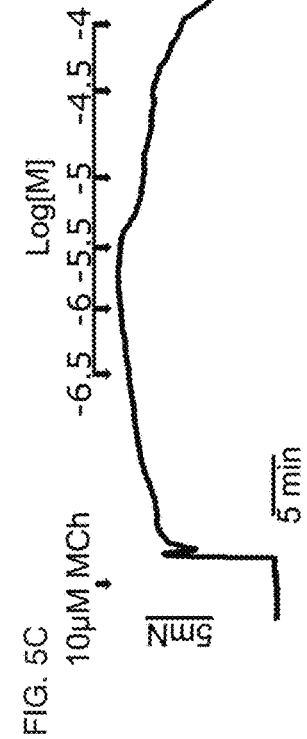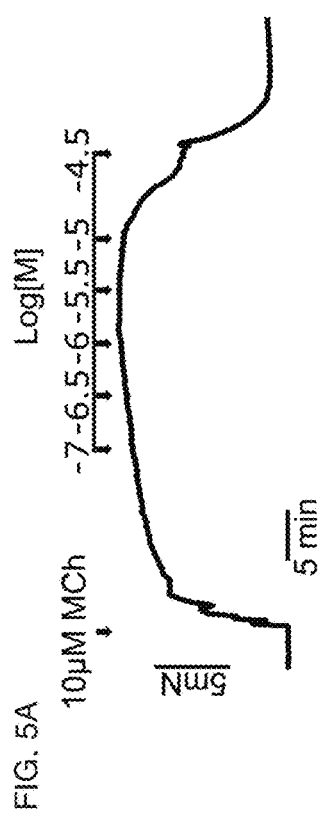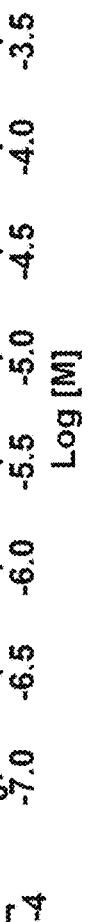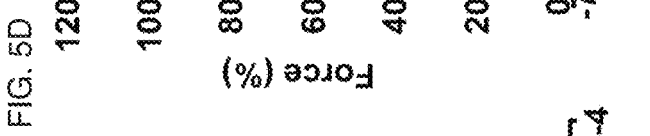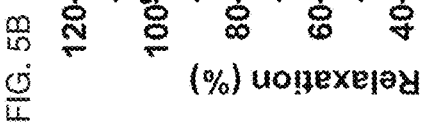
FIG. 5A  FIG. 5B  FIG. 5C  FIG. 5D

METHODS AND COMPOSITIONS FOR TREATMENT OF COPD DISEASES

CROSS REFERENCE TO RELATED PATENT APPLICATIONS

This application is a continuation application of U.S. patent application Ser. No. 15/129,965, filed Sep. 28, 2016, entitled "Methods and Compositions for Treatment of COPD Diseases". U.S. application Ser. No. 15/129,965 is a 35 U.S.C. § 371 national phase application of International Application Serial No. PCT/CN2015/076120, filed Apr. 9, 2015 (WO 2015/158216 A1). International Application Serial No. PCT/CN2015/076120 claims priority to U.S. Provisional Patent Application No. 61/979,149, filed on Apr. 14, 2014. Each of the application referenced above are hereby incorporated by reference in their entirety.

BACKGROUND

When a person inhales, air passes into lungs and flows through progressively smaller airways, which are surrounded by smooth muscles. When these smooth muscles are in a pathological condition (e.g., swelling, constriction, etc.), various pulmonary diseases may result such as, for example, asthma. Asthma affects about 300 million people worldwide, and current therapeutic methods for treating asthma include immunological modulation, anti-inflammation, and relaxation of airway smooth muscle. Hormones or their derivatives (e.g., glucocorticoid, beta-adrenogenic agonists) are generally used in these therapeutic methods. However, uses of hormones and these derivatives might have risk of toxicity to liver, kidney and other organs.

SUMMARY

Embodiments of the present disclosure relate to a method for treating diseases, for example, a pulmonary disease. The method may include administering to a subject in need thereof a therapeutically effective amount of a compound of formula (I):

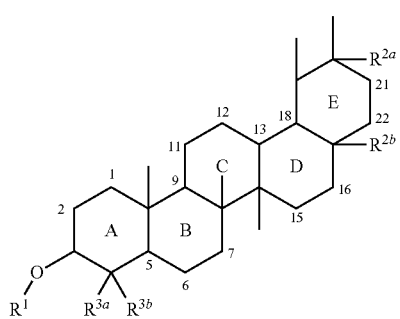

I wherein the A, B, C, D, or E ring is independently fully saturated or partially saturated, $R^1$ is selected from hydrogen or a carbohydrate residue, C2, C11, C12, and C19 are each independently substituted with hydrogen or —OH, $R^{2a}$ and $R^{2b}$ are selected from hydrogen, —COOH, or $COOR^4$, or together form —CO2-, $R^4$ is a certain monosaccharide residue, $R^{3a}$ and $R^{3b}$ together form $CH_2$, or are each independently selected from —$CH_3$ or —$CH_2$—OH, as a stereoisomer, enantiomer or tautomer thereof, or a pharmaceutically acceptable salt thereof.

Embodiments of the present disclosure also relate to a kit for treating diseases, for example, a pulmonary disease. The kit may include an amount of the compound of formula (I), wherein the A, B, C, D, or E ring is independently fully saturated or partially saturated, $R^1$ is selected from hydrogen or a carbohydrate residue, C2, C11, C12, and C19 are each independently substituted with hydrogen or —OH, $R^{2a}$ and $R^{2b}$ are selected from hydrogen, —COOH, or $COOR^4$, or together form —CO2-, $R^4$ is a certain monosaccharide residue, $R^{3a}$ and $R^{3b}$ together form $CH_2$, or are each independently selected from —$CH_3$ or —$CH_2$—OH, as a stereoisomer, enantiomer or tautomer thereof, or a pharmaceutically acceptable salt thereof. In certain embodiments, the compound of formula (I) is capable of treating the pulmonary disease. In certain embodiments, the compound of formula (I) is in a pharmaceutically acceptable carrier.

In some embodiments, the disease may include a pulmonary disease, which may include at least one of asthma, chronic obstructive pulmonary disease (COPD), bronchitis, chronic or acute bronchoconstriction, adult respiratory distress syndrome, acute lung injury, and bronchiectasis. In particular embodiments, the pulmonary disease may include asthma or COPD.

In some embodiments, the A and B rings are independently fully saturated, and $R^{2a}$ and $R^{2b}$ together form —CO2-.

In some embodiments, the carbohydrate residue is a monosaccharide residue or an oligosaccharide residue. In some embodiments, the certain carbohydrate residue is a monosaccharide residue or an oligosaccharide residue. In certain embodiments, the monosaccharide may be arabinose (Ara), glucuronic acid (GlcA) or 2-deoxy-glucuronic acid, glucose (Glc), or rhamnose (Rha). In certain embodiments, the oligosaccharide residue may be a disaccharide residue, a trisaccharide residue, or a tetrasaccharide residue.

In certain embodiments, the A, B, C, and E rings are fully saturated, the D ring is partially saturated, the C12 and C19 are each independently substituted with —OH, C15 and C16 are each independently substituted with two hydrogens, $R^{2a}$ and $R^{2b}$ together form —CO2-, $R^{3a}$ and $R^{3b}$ are —$CH_3$, $R^1$ is a monosaccharide residue or an oligosaccharide residue. In particular embodiments, $R^1$ is a trisaccharide residue. For example, the trisaccharide residue may be -Ara-[(1-2)-Rha]-(1-3)-Glc.

In certain embodiments, the A, B, C, and E rings are fully saturated, the D ring is partially saturated, the C12 and C19 are each independently substituted with —OH, C15 and C16 are each independently substituted with two hydrogens, $R^{2a}$ and $R^{2b}$ together form —CO2-, $R^{3a}$ and $R^{3b}$ are —$CH_3$, and $R^1$ is a monosaccharide residue or an oligosaccharide residue. In particular embodiments, $R^1$ is a tetrasaccharide residue. For example, the tetrasaccharide residue may be -Ara-[(1-2)-Rha]-(1-3)-Glc-(1-2)-Glc.

In certain embodiments, the A, B, C, and E rings are fully saturated, the D ring is partially saturated, the C11 and C19 are each independently substituted with —OH, C11 is substituted with hydrogen, $R^{2a}$ and $R^{2b}$ together form —CO2-, $R^{3a}$ and $R^{3b}$ are —$CH_3$, and $R^1$ is a monosaccharide residue or an oligosaccharide residue. In particular embodiments, $R^1$ is a trisaccharide residue. For example, the trisaccharide residue may be -Ara-[(1-2)-Rha]-(1-3)-Glc.

In certain embodiments, the A, B, and E rings are fully saturated, the C and D rings are partially saturated, the C19 is substituted with —OH, C9 is substituted with hydrogen, $R^{2a}$ and $R^{2b}$ together form —CO2-, $R^{3a}$ and $R^{3b}$ are —$CH_3$, and $R^1$ is a monosaccharide residue or an oligosaccharide residue. In particular embodiments, $R^1$ is a trisaccharide residue. For example, the trisaccharide residue may be -Ara-[(1-2)-Rha]-(1-3)-Glc.

In some embodiments, the compound of formula (I) is isolated from an extract of *kudingcha* (KE). In some embodiments, the subject is a human.

In some embodiments, the method may include delivering the therapeutically effective amount of the compound of formula (I) to an airway of a lung of the subject. In certain embodiments, the method may include delivering the therapeutically effective amount of the compound of formula (I) to an airway of a lung of the subject via inhalation of the compound of formula (I) by the subject.

In some embodiments, the kit may include a delivery device such as, for example, a spray device or a pressurized delivery device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 1A illustrates the extracts from n-butanol phase, FIG. 1B illustrates the extracts from ethyl acetate phase, FIG. 1C illustrates extracts from water phase, and FIG. 1D shows the quantitation for the relaxation (Bars represent mean±SEM, n=4).

FIG. 2A illustrates the percentage of airway resistance after inhaling n-BuOH phase and albuterol, and FIG. 2B illustrates the quantitation of airway resistance at 3 minutes after challenge (Bars represent mean±SEM, n=8).

FIGS. 5A-D illustrate that Kudinoside A and D relaxe bronchial rings with a dose-dependent manner. FIGS. 5A-B illustrate the reduced force responses of airway bronchial rings to Kudinoside D, while the airway smooth muscle is stimulated with methacholine. FIGS. 5C-D illustrate the reduced force responses of airway bronchial rings to Kudinoside A.

FIG. 6A illustrates time course of decreased airway resistance within 5 min in response to PBS, 0.03 µg Kudinoside D, 0.31 µg Kudinoside D, 3 µg Kudinoside D and 3 µg albuterol respectively. FIG. 6B illustrates the statistical analysis of the relative percentage of airway resistance decreased at 3 min after giving these reagents (**P<0.01 versus PBS. Bars represent mean±SEM).

FIG. 8A illustrates 50 µM Kudinoside A, FIG. 8B illustrates the Organic Phase, and FIG. 8C illustrates the Water Phase.

FIG. 9A illustrates the recordings of three primary airway smooth muscle cells under vehicle, 50 µM Kudinosdie A and 1 µM Nifedipine treatment, respectively. FIG. 9B illustrates the current-voltage relationship for peak currents in Vehicle (circle curve), 50 µM Compound A (squire curve) and 1 µM Nifedipine (triangle curve).

DETAILED DESCRIPTION

Overview

Figure 1A:
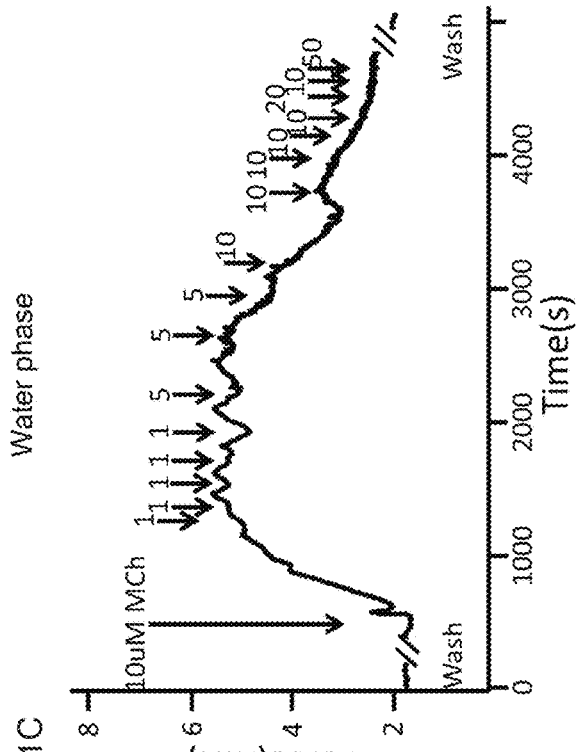
FIGS. 1A-D illustrates relaxation of airway smooth muscle by *kudingcha* extracts. After extraction with different solvents, the extracts were dissolved with equal volume of ethanol. The bronchial segments were evoked by 10 µM MCh and relaxed with accumulated addition of extracts.

Embodiments of the present disclose contemplate a use of *kudingcha* extracts and/or derivatives of the *kudingcha* extracts for treating pulmonary diseases (e.g., asthma, chronic obstructive pulmonary disease (COPD), etc.) on a subject. The present disclosure relates, in part, to the demonstration that *kudingcha* extracts and/or derivatives of the *kudingcha* extracts may relax smooth muscles of airways and relieve the symptoms associated with pulmonary diseases on the subject. For example, as shown in the accompanying embodiments, *kudingcha* extracts (e.g., kudinoside A, kudinoside D, etc.) may relax airway smooth muscle and reduce asthmatic constriction.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of". Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "alkyl" (alone or in combination with another term(s)) refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are referred to as lower alkyl groups. When said lower alkyl groups lack substituents, they are referred to as unsubstituted lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like. The alkyl group may be substituted or unsubstituted. When substituted, the substituent group(s) is preferably one or more, more preferably one to three, even more preferably one or two substituent(s) independently selected from the group consisting of halo, hydroxy, unsubstituted lower alkoxy, aryl optionally substituted with one or more groups, preferably one, two or three groups which are independently of each other halo, hydroxy, unsubstituted lower alkyl or unsubstituted lower alkoxy groups, aryloxy optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 5- or 6-member heterocyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, mercapto, (unsubstituted lower alkyl)thio, arylthio optionally substituted with one or more groups, preferably one, two or three groups which are independently of each other halo, hydroxy, unsubstituted lower alkyl or alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)O—, and —NR$_{13}$R$_{14}$, wherein R$_{13}$ and R$_{14}$ are independently selected from the group consisting of hydrogen, unsubstituted lower alkyl, trihalomethyl, cycloalkyl, heterocyclic and aryl optionally substituted with one or more, groups, preferably one, two or three groups which are independently of each other halo, hydroxy, unsubstituted lower alkyl or unsubstituted lower alkoxy groups.

Preferably, the alkyl group is substituted with one or two substituents independently selected from the group consisting of hydroxy, 5- or 6-member heterocyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, or —NR$_{13}$R$_{14}$, wherein R$_{13}$ and R$_{14}$ are independently selected from the group consisting of hydrogen and alkyl. Even more preferably the alkyl group is substituted with one or two substituents which are independently of each other hydroxy, dimethylamino, ethylamino, diethylamino, dipropylamino, pyrrolidino, piperidino, morpholino, piperazino, 4-lower alkylpiperazino, phenyl, imidazolyl, pyridinyl, pyridazinyl, pyrimidinyl, oxazolyl, triazinyl, and the like.

As used herein, the term "aromatic", "ar" or "aryl" (alone or in combination with another term(s)) refer to aromatic cyclic groups (for example 6 membered monocyclic, 10 membered bicyclic or 14 membered tricyclic ring systems) which contain 6 to about 14 carbon atoms. Exemplary aromatic groups include phenyl, naphthyl, biphenyl, indenyl, and anthracene.

As used herein, the term "halogen" (alone or in combination with another term(s)) refers to a fluorine substituent ("fluoro", which may be depicted as —F), chlorine substituent ("chloro", which may be depicted as —Cl), bromine substituent ("bromo", which may be depicted as —Br), or iodine substituent ("iodo", which may be depicted as —I).

As used herein, the term "cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system.

Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. When substituted, the substituent group(s) is preferably one or more, more preferably one or two substituents, independently selected from the group consisting of unsubstituted lower alkyl, trihaloalkyl, halo, hydroxy, unsubstituted lower alkoxy, aryl optionally substituted with one or more, preferably one or two groups independently of each other halo, hydroxy, unsubstituted lower alkyl or unsubstituted lower alkoxy groups, aryloxy optionally substituted with one or more, preferably one or two groups independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more, preferably one or two groups independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, unsubstituted lower alkyl or unsubstituted lower alkoxy groups, 5- or 6-member heterocyclic group having from 1 to 3 heteroatoms selected from the group consisting of nitrogen, oxygen and sulfur, the carbon and nitrogen (if present) atoms in the group being optionally substituted with one or more, preferably one or two groups independently of each other halo, hydroxy, unsubstituted lower alkyl or unsubstituted lower alkoxy groups, mercapto, (unsubstituted lower alkyl)thio, arylthio optionally substituted with one or more, preferably one or two groups independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$ are as defined above.

As used herein, the term "alkenyl" (alone or in combination with another term(s)) refers to a lower alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

As used herein, the term "alkynyl" (alone or in combination with another term(s)) refers to a lower alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$, with R$_{13}$ and R$_{14}$ as defined above. Preferably, the aryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "heteroaryl" refers to a monocyclic or fused ring (i.e., rings which share an adjacent pair of atoms) group of 5 to 12 ring atoms containing one, two, or three ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more, more preferably one, two, or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$, with R$_{13}$ and R$_{14}$ as defined above. Preferably, the heteroaryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "Heterocyclic" refers to a monocyclic or fused ring group having in the ring(s) of 5 to 9 ring atoms in which one or two ring atoms are heteroatoms selected from N, O, or S(O)n (where n is an integer from 0 to 2), the remaining ring atoms being C. The rings may also have one or more double bonds. However, the rings do not have a completely conjugated pi-electron system. Examples, without limitation, of unsubstituted heterocyclic groups are pyrrolidino, piperidino, piperazino, morpholino, thiomorpholino, homopiperazino, and the like. The heterocyclic ring may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl) thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$, with R$_{13}$ and R$_{14}$ as defined above. Preferably, the heterocyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

Preferably, the heterocyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "Hydroxy" refers to an —OH group.

As used herein, the term "Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

As used herein, the term "Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

The terms "heterocycle", "heterocyclic" or "heterocyclo" (alone or in combination with another term(s)) refer to fully saturated (i.e., "heterocycloalkyl"), non-aromatic partially-saturated (i.e., "heterocycloalkenyl"), or heterocylic aromatic (i.e. "heteroaryl") ring structure, typically having 3 to about 20 carbon atoms, more typically having 3 to about 14 carbon atoms. For example, the heterocyclic group may a 4 to about 7 membered monocyclic ring systems, a 7 to about 11 membered bicyclic ring systems, or a 10 to about 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isothiazolyl, thiadiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6-oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyi"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

A heterocyclyl alternatively may be from 2 to 5 (more typically from 2 or 3) rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the multi-ring heterocyclyls are indolizinyl, pyranopyrrolyl, purinyl, pyridopyridinyl, pyrindinyl, and 4H-quinolizinyl.

Exemplary bicyclic heterocyclic groups include indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyll or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl", "thionaphthenyl" and "benzothiofuranyl"), isobenzothienyl (also known as "isobenzothiophenyl", "isothionaphthenyl" and "isobenzothiofuranyl"), benzothiazolyl, benzoisothiazolyl, benzothiadiazolyl, benzoxadiazolyl, indolyl, isoindazolyl (also known as "benzopyrazolyl"), benzoimidazolyl, benzotriazolyl, benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzoxadiazinyl, and xanthenyl. In some embodiments, the benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

As used herein, the term "heteroaryl" (alone or in combination with another term(s)) refers to an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiadiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazolyl, carbazolyl, and acridinyl. In some embodiments, the 5-membered rings include furanyl, thienyl, oxazolyl, isoxazolyl, thiazolyl, isothiazolyl, oxadiazolyl, pyrazolyl, and imidazolyl; the 6-membered rings include pyridinyl, pyrazinyl, pyrimidinyl, pyridazinyl, and triazinyl; the 6/5-membered fused-ring systems include benzoxazolyl, benzoisoxazolyl, anthranilyl, benzothienyl, isobenzothienyl, and purinyl; and the 6/6-membered fused-ring systems include quinolinyl, isoquinolinyl, and benzodiazinyl.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

As used herein, the term "hydrogen" (alone or in combination with another term(s)) refers to a hydrogen substituent and may be depicted as —H.

As used herein, the term "hydroxy" (alone or in combination with another term(s)) refers —OH.

As used herein, the term "nitro" (alone or in combination with another term(s)) refers to —$NO_2$.

As used here, "carbohydrate" is a compound containing one or more monosaccharide residues. A monosaccharide may be a polyhydroxy aldehyde such as D-glucose or a polyhydroxy ketone such as D-fructose. Monosaccharides may be classified according to the number of carbons they contain: monosaccharides with three carbons are trioses, those with four carbons are tetroses, those with five carbons are pentoses, and those with six and seven carbons are hexoses and heptoses, respectively. For example, a six-carbon polyhydroxy aldehyde such as D-glucose is an aldohexose, whereas a six-carbon polyhydroxy ketone such as D-fructose is a ketohexose. Monosaccharide may be present in different diasteromeric forms, such as α or β anomers, and D or L isomers. In some embodiments, monosaccharides may include unsubstituted saccharides such as glucose or galactose, as well as modified saccharides in which one or more hydroxyl groups contain substitutions or have been replaced with hydrogen or substituted carbon atoms (e.g., sialic acid)

An "oligosaccharide" refers to a short chain of covalently linked monosaccharide units (i.e., 2 to 9 monosaccharide units). For example, oligosaccharides include disaccharides each including two monosaccharide units, trisaccharides each including three monosaccharide units, and tetrasaccharide each including four monosaccharide units. A "polysaccharide" consists of long chains of covalently linked monosaccharide units (i.e., more than 10 monosaccharide units). A oligosaccharide and polysaccharide may include linear chain or branched chains with various combinations of monosaccharide units. In particular embodiments, the linear chain or branched chains with various combinations of Glc, Ara, Rha and GlcA, wherein Glc is glucose, Ara is arabinose, GlcA is glucuronic acid, and Rha is rhamnose.

Portions of a carbohydrate molecule may include non-saccharide groups such as, for example, anti-idiotypic antibodies or cyclohexane derivatives that mimic the structure of a monosaccharide residue. For example, a compound that mimics a structure of monosaccharide residues but that contains few or no monosaccharide residues may be determined using a computer three dimensional modeling programs such as, for example, the model of Hricouini et al., Biochem. 31:10018-10023 (1992). As used here, a monosaccharide residue may include a monosaccharide residue or a non-saccharide group that mimics the structure of the monosaccharide residue. A disaccharide residue may include a disaccharide residue or a non-saccharide group that mimics the structure of the disaccharides residue. An oligosaccharide residue may include a oligosaccharide residue or a non-saccharide group that mimics the structure of the oligosaccharides residue.

As used herein, the term "substitution" refers to a compound having a substituent comprising at least one carbon, nitrogen, oxygen, or sulfur atom that is bonded to one or more hydrogen atoms. If a substituent is described as being "substituted", a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, monofluoroalkyl is alkyl substituted with a fluoro, and difluoroalkyl is alkyl substituted with two fluoros. It should be recognized that if there are more than one substitutions on a substituent, each non-hydrogen substituent may be identical or different (unless otherwise stated).

If a substituent is described as being "optionally substituted", the substituent is either (1) substituted, or (2) not substituted. When the members of a group of substituents are described generally as being optionally substituted, any atom capable of substitution in each member of such group may be (1) substituted, or (2) not substituted. Such a characterization contemplates that some members of the group are not substitutable. Atoms capable of substitution include, for example, carbon bonded to at least one hydrogen, oxygen bonded to at least one hydrogen, sulfur bonded to at least one hydrogen, or nitrogen bonded to at least one hydrogen. On the other hand, hydrogen alone, halogen, oxo, and cyano do not fall within the definition of being capable of substitution.

"Stable compound" and "stable structure" are meant to indicate a compound that is sufficiently robust to survive isolation to a useful degree of purity from a reaction mixture, and formulation into an efficacious therapeutic agent.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals. In some embodiments, a pharmaceutically acceptable carrier may include one or more inactive pharmaceutical ingredients. The inactive pharmaceutical ingredients in the pharmaceutically acceptable carrier system may include stabilizers, preservatives, additives, adjuvants, aerosols, compressed air or other suitable gases, or other suitable inactive pharmaceutical ingredients formulated with the therapeutic compound (i.e., an active ingredient (API)).

The pharmaceutically acceptable carrier (e.g., inhalation carrier) may include the pharmaceutically suitable inactive ingredients known in the art for use in various inhalation dosage forms, such as aerosol propellants (e.g., hydrofluoroalkane propellants), surfactants, additives, suspension agents, solvents, stabilizers and the like. Alcohol is a good example of an ingredient that may be considered either active or inactive depending on the product formulation.

As used herein, inhalation dosage forms include, but are not limited to, an aerosol being a drug product that is packaged under pressure and contains the API and carrier system that are released upon activation of an appropriate valve system intended for topical application to the olfactory epithelium. The inhalation dosage form may also be delivered to mouth (lingual and sublingual aerosols), or lungs (inhalation aerosols); foam aerosol being a dosage form containing one or more APIs, surfactants, aqueous or non-aqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged; metered aerosol being a pressurized dosage form for use with metered dose valves which allow for the delivery of a uniform quantity of spray upon each activation; powder aerosol being a product that is packaged under pressure and contains APIs, in the form of a powder, that are released upon activation of an appropriate valve system; and, aerosol spray being an aerosol product which utilizes a compressed gas as the propellant to provide the force necessary to expel the product as a wet spray and being applicable to solutions of medicinal agents in aqueous solvents.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromicacid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, 5 ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Substantially" means nearly totally or completely, for instance, 95%, 96%, 97%, 98%, 99% or greater of some given quantity.

As used herein, the terms "treating" and "treatment" are used to refer to administration or application of a therapeutic agent to a subject or performance of a procedure or modality on a subject for the purpose of obtaining a therapeutic benefit of a disease or health-related condition, and includes: (1) preventing the disease or condition from occurring in a mammal, in particular, when such mammal is predisposed to the condition but has not yet been diagnosed as having it; (2) inhibiting the disease or condition, i.e., arresting its development; (3) relieving the disease or condition, i.e., causing regression of the disease or condition; or (4) relieving the symptoms resulting from the disease or condition, i.e., relieving pain without addressing the underlying disease or condition. For example, treatment of a subject with asthma or COPD may include reducing a frequency, and/or severity of one or more symptoms (e.g., dyspnea, wheezing, cough, chest discomfort, nasal congestion, etc.) associated with asthma, COPD, etc.

As used herein, the terms "preventing," "inhibiting," "reducing" or any variation of these terms, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99% or more, or any range derivable therein, reduction of activity or symptoms, compared to normal.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. For example, a disease and/or condition in the present disclosure may include asthma, chronic or acute bronchoconstriction, chronic bronchitis, small airways obstruction, and emphysema, obstructive or inflammatory airways diseases (e.g., chronic eosinophilic pneumonia, chronic obstructive pulmonary disease (COPD), etc.), bronchitis, acute lung injury, bronchiectasis, etc.

As used herein, the terms "administered" and "delivered" are used to describe the process by which a composition of the present disclosure is administered or delivered to a subject, a target (e.g., a cell, a tissue, an organ, a portion of a system, etc.) or are placed in direct juxtaposition with the target. In some embodiments, "administrated" and "delivered" may include a process that inhalation of a subject such that a composition of the present disclosure is delivered to the subject, a target (e.g., a cell, a tissue, an organ, a portion of a system, etc.) or are placed in direct juxtaposition with the target. In some embodiments, a composition of the present disclosure may be administered orally, intravenously, intraperitoneally, subcutaneously, intramuscularly, intrathecally, intradermally, nasally, enterically, pessaries, suppositories. For example, a target may be an airway smooth muscle fiber or a portion of an airway of a subject. The terms "administered" and "delivered" are used interchangeably.

As used herein, the terms "contacted" and "exposed" when applied to a target (e.g., a cell, a tissue, an organ, etc.), are used to describe the process by which a compound of the present disclosure is administered or delivered to a target or are placed in direct juxtaposition with the target. The terms "administered" and "delivered" are used interchangeably with "contacted" and "exposed".

As used herein, the terms "patient", "subject" and "individual" are used interchangeably herein, and mean a mammalian subject to be treated and/or to obtain a biological sample from the mammalian subject. The mammalian includes humans and domestic animals, such as cats, dogs, swine, cattle, sheep, goats, horses, rabbits, and the like.

As used herein, the term "effective" means adequate to accomplish a desired, expected, or intended result. For example, an "effective amount" may be an amount of a compound sufficient to produce a therapeutic benefit.

As used herein, the terms "therapeutically effective" or "therapeutically beneficial" refers to anything that promotes or enhances the well-being of the subject with respect to the medical treatment of a condition. This includes, but is not limited to, a reduction in the onset, frequency, duration, or severity of the signs or symptoms of a disease.

As used herein, the term "therapeutically effective amount" is meant an amount of a composition as described herein effective to yield the desired therapeutic response. The amount of a compound of the disclosure which constitutes a "therapeutically effective amount" will vary depending on the compound, the condition and its severity, and the age of the mammal to be treated, but can be determined routinely by one of ordinary skill in the art having regard to her own knowledge and to this disclosure.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations", 2nd Ed., Academic Press, New York. 1983; H. O. House, "Modem Synthetic Reactions", 2nd Ed., W. A. Benjamin, Inc. Menlo Park, Calif. 1972; T. L. Gilchrist. "Heterocyclic Chemistry", 2nd Ed., John Wiley & Sons, New York, 1992; 1. March, "Advanced Organic Chemistry: Reactions, Mechanisms and Structure", 4th Ed., Wiley Interscience, New York, 1992. Specific and analogous reactants may also be identified through the indices of known chemicals prepared by the Chemical Abstract Service of the American Chemical Society' which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

As used herein, the terms "diagnostic", "diagnose" and "diagnosed" mean identifying the presence or nature of a pathologic condition.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used as described herein. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

Multiple compounds of the disclosure have a central nucleus of five rings (i.e., a core structure), designated herein as A, B, C, D, and E as shown below:

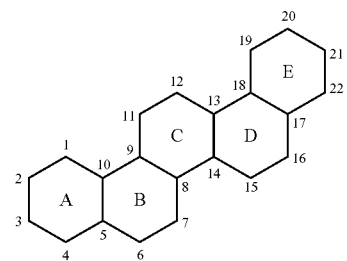

The carbons of the central nucleus are numbered as set forth above. For purposes herein, the carbon at position 1 of the central nucleus is indicated herein as C 1, and so forth. In the compounds of the disclosure, unless otherwise indicated, each of rings A, B, C, D and E is independently fully saturated, partially saturated or fully unsaturated. That is, hydrogens attached to any of the carbons at positions 1-22 may be omitted so as to allow unsaturation within the A, B, C, D, and/or E rings.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein for the compounds of the disclosure is a modified form of the I.U.P.A.C. nomenclature system, using the ChemDoodle Version 6.0.0 software program, wherein multiple compounds are named herein as derivatives of the core structure described above. In addition, the configuration of the substituents are indicated in the names of the compounds by an "α" if the substituent is below the plane of the indene ring and by a "β" is the substituent is above the plane of the indene ring. For example, a compound of formula (Ia) (showing the numbering of the carbons):

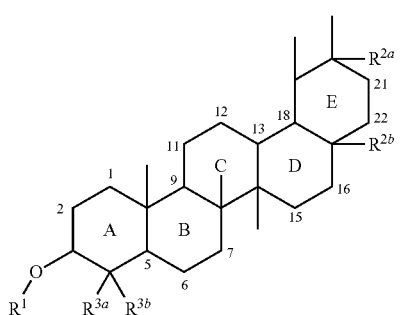

Ia

Wherein the A, B, D, and E ring are independently fully saturated; the C ring is partially saturated; C2, C3, C5, C9, C10, C11, C12, C18, and C20 are each independently substituted with hydrogen; C1, C7, C8, C11, C15, C16, C19, C21, and C22 are substituted with two hydrogens; $R^1$ and $R^{2a}$ each are independently hydrogen; C2 is substituted with —OH, $R^{2b}$ is —COOH, and $R^{3a}$ and $R^{3b}$ together form methylene, i.e., a compound of the following formula (Ib):

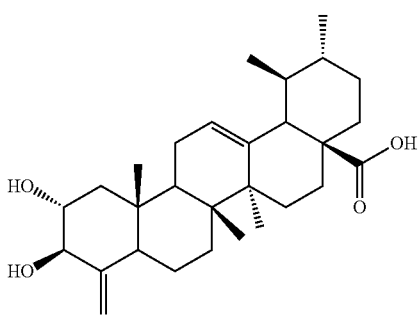

Ib is named herein as (1S,2R,5S,8S,9R,14R,15R,17R)-10,11-Dihydroxy-1,2,6a,6b,12a-pentamethyl-9-methylene-2,3,4,4a,5,6,6a,6b,7,8,8a,10,11,12,12a,12b,13,14b-octadecahydro-1H-picene-4a-carboxylic acid. The common name of the compound is Ilekudinol B with a ChemSpider database ID: 8822838.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

Tautomers refer to various forms of a compound that differ only by the shifting of one or more double bonds and the concomitant shifting of hydrogen atoms. The present disclosure includes tautomers of any said compounds.

Methods and Compositions for Treatment of Diseases

Embodiments of the present disclosure relate to a method for treating diseases, for example, a pulmonary disease. The method may include administering to a subject in need thereof a therapeutically effective amount of a compound of formula (I):

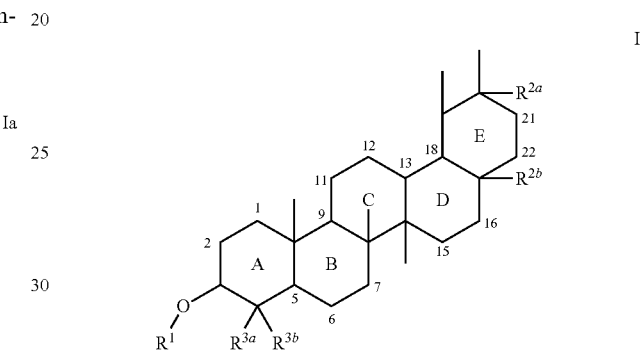

I wherein the A, B, C, D, or E ring is independently fully saturated or partially saturated, $R^1$ is selected from hydrogen or a carbohydrate residue, C2, C11, C12, and C19 are each independently substituted with hydrogen or —OH, $R^{2a}$ and $R^{2b}$ are selected from hydrogen, —COOH, or $COOR^4$, or together form —CO2-, $R^4$ is a certain monosaccharide residue, $R^{3a}$ and $R^{3b}$ together form $CH_2$=, or are each independently selected from —$CH_3$ or —$CH_2$—OH, as a stereoisomer, enantiomer or tautomer thereof, or a pharmaceutically acceptable salt thereof.

Embodiments of the present disclosure also relate to a kit for treating diseases, for example, a pulmonary disease. The kit may include an amount of the compound of formula (I), wherein the A, B, C, D, or E ring is independently fully saturated or partially saturated, $R^1$ is selected from hydrogen or a carbohydrate residue, C2, C11, C12, and C19 are each independently substituted with hydrogen or —OH, $R^{2a}$ and $R^{2b}$ are selected from hydrogen, —COOH, or $COOR^4$, or together form —CO2-, $R^4$ is a certain monosaccharide residue, $R^{3a}$ and $R^{3b}$ together form $CH_2$=, or are each independently selected from —$CH_3$ or —$CH_2$—OH, as a stereoisomer, enantiomer or tautomer thereof, or a pharmaceutically acceptable salt thereof. In certain embodiments, the compound of formula (I) is capable of treating the pulmonary disease. In certain embodiments, the compound of formula (I) is in a pharmaceutically acceptable carrier.

In some embodiments, the disease may include a pulmonary disease, which may include at least one of asthma, chronic obstructive pulmonary disease (COPD), bronchitis, chronic or acute bronchoconstriction, adult respiratory distress syndrome, acute lung injury, and bronchiectasis. In particular embodiments, the pulmonary disease may include asthma or COPD.

Chronic obstructive pulmonary disease (COPD) includes a condition in which there is limited airflow in the lungs. COPD may develop and worsens over time, and result in changes in the small airways of a subject with COPD. These changes cause walls to narrow during expiration, making the subject hard to breathe. In certain subjects, the small sacs where oxygen and carbon dioxide are exchanged are destroyed, gradually starving the body of oxygen. COPD may be associated with a set of breathing-related symptoms, for example, being out of breath, chronic cough, spitting or coughing mucus (phlegm), the ability to exhale (breathe in) getting worse over time. COPD may have three forms: emphysema, chronic bronchitis, and obstructive bronchiolitis. The emphysema may be marked by destruction of the alveoli, grape-like clusters of air sacs at the end of the smallest airways (the bronchioles) in the lung. The chronic bronchitis may be defined as coughing and overproduction of mucus for a threshold time during a predetermined time period. The obstructive bronchiolitis involve an inflammatory condition of the small airways. COPD may also be called as chronic obstructive airways disease, Chronic obstructive lung disease, Chronic bronchitis, Emphysema, Bronchitis-chronic. Smoking may cause COPD while other reasons may also lead to COPD. For example, a subject who lacks alpha-1 antitrypsin or is exposed to certain gases, fumes or dust may develop COPD. One of the tests for COPD is a lung function test called spirometry, which involves blowing out as hard as possible into a small machine that tests lung capacity. In some instances, using a stethoscope to listen to lungs, pictures of lungs, blood tests may be used for determination of COPD.

Asthma includes a pulmonary condition that makes a subject with asthma difficult to breathe properly. For example, in response to allergens or other environmental triggers, the airways of the subject may undergo changes. The changes appear to be two specific responses hyperreactive response (also called hyperresponsiveness) and inflammatory response. These responses in the airways cause coughing, wheezing, shortness of breath (dyspnea), or other symptoms of asthma. Asthma shares some of the symptoms of COPD (e.g., chronic coughing, wheezing, shortness of breath, etc.), and a subject may have asthma and COPD at the same time. For example, roughly 40% of known COPD suffers also have asthma. Asthma may include various types of asthma such as, e.g., atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitis asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome, bronchiolytis, etc. In particular embodiments, asthma may include allergenic asthma.

Bronchitis includes bronchitis of various types, etiologies, or pathogenesis. For example, bronchitis may include acute bronchitis, acute laryngotracheal bronchitis, arachidic bronchitis, catarrhal bronchitis, croupous bronchitis, dry bronchitis, infectious asthmatic bronchitis, productive bronchitis, *Staphylococcus* or streptococcal bronchitis, vesicular bronchitis, etc.

Bronchiectasis includes bronchiectasis of various types, etiology, or pathogenesis. For example, bronchiectasis may include cylindric bronchiectasis, sacculated bronchiectasis, fusiform bronchiectasis, capillary bronchiectasis, cystic bronchiectasis, dry bronchiectasis, follicular bronchiectasis, etc. Bronchiectasis may include a condition that a subject receiving treatment of smooth muscle relaxation, which may also related to COPD.

Bronchconstriction may include a condition related to the constriction of the airways in the lungs due to the tightening of the surrounding smooth muscle which causes cough, wheezing and shortness of breath. Chronic bronchoconstriction may be caused by chronic obstructive pulmonary disease, and acute bronchoconstriction may be caused by acute inducer of obstructive pulmonary diseases, e.g. exercise, dust, and drug-induced bronchoconstriction.

Acute respiratory distress syndrome (ARDS), a lung syndrome that may cause inflammation of the lung parenchyma leading to impaired gas exchange with a systemic release of inflammatory mediators, causing inflammation, hypoxemia and frequently multiple organ failure.

In some embodiments, the disease may include hypertension, gastrointestinal motility, or other smooth muscle diseases.

In some embodiments, the A and B rings are independently fully saturated, and $R^{2a}$ and $R^{2b}$ together form —CO2-.

In some embodiments, the carbohydrate residue is a monosaccharide residue or an oligosaccharide residue. In some embodiments, the certain carbohydrate residue is a monosaccharide residue or an oligosaccharide residue. In certain embodiments, the monosaccharide may be arabinose (Ara), glucuronic acid (GlcA) or 2-deoxy-glucuronic acid, glucose (Glc), or rhamnose (Rha). In certain embodiments, the oligosaccharide residue may be a disaccharide residue, a trisaccharide residue, or a tetrasaccharide residue.

In certain embodiments, the A, B, C, and E rings are fully saturated, the D ring is partially saturated, the C12 and C19 are each independently substituted with —OH, C15 and C16 are each independently substituted with two hydrogens, $R^{2a}$ and $R^{2b}$ together form —CO2-, $R^{3a}$ and $R^{3b}$ are —CH$_3$, $R^1$ is a monosaccharide residue or an oligosaccharide residue. In particular embodiments, $R^1$ is a trisaccharide residue. For example, the trisaccharide residue may be -Ara-[(1-2)-Rha]-(1-3)-Glc.

In certain embodiments, the A, B, C, and E rings are fully saturated, the D ring is partially saturated, the C12 and C19 are each independently substituted with —OH, C15 and C16 are each independently substituted with two hydrogens, $R^{2a}$ and $R^{2b}$ together form —CO2-, $R^{3a}$ and $R^{3b}$ are —CH$_3$, and $R^1$ is a monosaccharide residue or an oligosaccharide residue. In particular embodiments, $R^1$ is a tetrasaccharide residue. For example, the tetrasaccharide residue may be -Ara-[(1-2)-Rha]-(1-3)-Glc-(1-2)-Glc.

In certain embodiments, the A, B, C, and E rings are fully saturated, the D ring is partially saturated, the C11 and C19 are each independently substituted with —OH, C11 is substituted with hydrogen, $R^{2a}$ and $R^{2b}$ together form —CO2-, $R^{3a}$ and $R^{3b}$ are —CH$_3$, and $R^1$ is a monosaccharide residue or an oligosaccharide residue. In particular embodiments, $R^1$ is a trisaccharide residue. For example, the trisaccharide residue may be -Ara-[(1-2)-Rha]-(1-3)-Glc.

In certain embodiments, the A, B, and E rings are fully saturated, the C and D rings are partially saturated, the C19 is substituted with —OH, C9 is substituted with hydrogen, $R^{2a}$ and $R^{2b}$ together form —CO2-, $R^{3a}$ and $R^{3b}$ are —CH$_3$, and $R^1$ is a monosaccharide residue or an oligosaccharide residue. In particular embodiments, $R^1$ is a trisaccharide residue. For example, the trisaccharide residue may be -Ara-[(1-2)-Rha]-(1-3)-Glc.

In some embodiments, the compound of formula (I) is isolated from an extract of *kudingcha* (KE). In certain embodiments, KE may include one or more solutions and/or compounds extracted from *kudingcha* using methods described in the present disclosure and/or methods known to one of ordinary skill in the art. The *kudingcha* may include, for example, *Ilex kudingcha*, x *latifolia*, *Ilex kaushue*, *Ilex pentagona*, *Ilex cornuta*, *Ilex paraguariensis*, *Ligustrum robustum*, etc., which may be collected from various places.

In some embodiments, the subject is a human. In other embodiments, the subject may be domestic animals, such as cats, dogs, swine, cattle, sheep, goats, horses, rabbits, and the like.

In some embodiments, the method may include delivering the therapeutically effective amount of the compound of formula (I) to an airway of a lung of the subject. In certain embodiments, the method may include delivering the therapeutically effective amount of the compound of formula (I) to an airway of a lung of the subject via inhalation of the compound of formula (I) by the subject.

In some embodiments, the kit may include a delivery device such as, for example, a spray device or a pressurized delivery device.

*kudingcha* and Extracts of *kudingcha*

*kudingcha* may be made of various plants. For example, the plants may include *Ligustrum purpurascens* Y. C. Yang, *Ligustrum pricei* Hayata, *Ligustrum japonicum* var. *pubescens* Koidz., *Ligustrum delavayanum* Hariot., *Ligustrum henryi* Hemsl., *Ligustrum lucidum* Ait., *Ilex kudingcha* C. J. Tseng, *Ilex latifolia* Thunb, *Ilex cornuta* Lindl., *Ilex pentagona* S. K. Chen, *Ilex kaushue* S. Y. Hu, *Ligustrum sinense* var. *myrianthum* (Diels) Hofk., *Ligustrum robustum* (Roxb.) Bl., *Cratoxylum formosum* subsp. *Pruniflorum* (Kurz) Gogelin, *Ehretia thyrsiflora* (Sieb. Et. Zucc.) Nakai., *Clerodendrum fortunatum* Linn., Mahonia (Fort) Carrie., *Itea ilicifolia* Oliver., etc. Among these plants, the widely used plants for *kudingcha* at the current time are *Ilex* plants, *Ilex kudingcha* C. J. Tseng, *Ilex pentagona* S. K. Chen, *Ilex huoshanensis* Y. H. He and *Ligustrum* (e.g. *Ligustrum robustum* (Roxb.) Bl., *Ligustrum henryi* Hemsl., *Ligustrum pricei* Hayata.

*kudingcha* may have various pharmaceutical activities in different systems. For example, in the vascular system, crude extracts of *kudingcha* may improve blood circulation of heart and brain, possibly due to the release of blood vessel tone through total saponins. In the heamoitic system, *kudingcha* extracts may inhibit platelet aggregation, reduce circulating lipid, regulate circulating glucose level, etc. *kudingcha* may also have efficacy on hyperlipidemia, and affect metabolism of the body. When drank as tea, *kudingcha* may reduce body weight by inhibiting adopocyte production, for example, via a mechanism associated with inhibition activity of *Ilex kudingcha* toward ACAT (Triterpenoidacyl CoA cholylacyl Transferase).

In the immune system, *kudingcha* extracts and saponins may be active in modulating the function of macrophage, lymphocytes, thereby inhibiting different inflammatory reactions. *kudingcha* as drinking tea may have an effect on vessel and skin inflammation.

In the respiratory system, the extracts of *Ilex latifolia* Thunb may inhibit airway smooth muscle contraction induced by external calcium, but the underlying mechanism and the identity of its active substance remain unknown. Extracts of *L. lucidum* Ait are effective in eliminating phlegm and inhibiting cough, but there is no clinical report of treating respiratory diseases, including asthma and other COPD diseases, with *L. lucidum* Ait.

In some embodiments, various groups of substances from *kudingcha* were identified, for example, a group of phenylpropanid compounds, flavonoids, terpenoids, essential oils, etc. The group of phenylpropanid compounds include ligupurpuroside A and B, etc. The group of flavonoids include quercetin, hyperoside, luteolin-7-glucoside etc. The group of terpenoids include monterpenes and triterpenes. Also, several compounds of triterpenes are also identified from *kudingcha* such as, for example, latifoloside B, C, N and O, siaresinolic acid, 24-hydroxyl-oleanolic acid, kudinoside A~T, ilekudinoside A~S, ilexoside XL VIII, oleanolic acid, beta-amyrin, olean-12-ene and kudingchagenin I. The group of essential oils are produced primarily from the young leaves.

Diseases and Smooth Muscle Contractility

Asthma includes a chronic disease of the lung characterized by episodic and occasionally persistent airflow obstruction. It causes substantial morbidity and occasional mortality among its sufferers. Nearly 300 million people all over the world suffer from asthma and it has brought striking social losses as well as economic losses. The featured syndromes of asthma may include shortness of breath, chest tightness, and coughing in asthmatic episodes. These syndromes of asthma may be triggered by the exposure to allergens, cold air, exercise or other irritants. The pathological alteration of asthma may be characterized by chronic inflammation, mucus hyperplasia, reversible airway obstruction, and airway hyperresponsiveness (AHR), in which hyperresponsiveness of airway smooth muscle contractility is believed to be a cause of airway constriction. AHR may be defined as an excessive airway narrowing in response to a variety of chemical and physical stimulus that have little or no effects in healthy subjects and is documented in vivo by leftward and upward shifts of the dose-response curve to constrictor agents. The increased sensitivity to stimuli may be usually caused by inflammatory reaction surrounding smooth muscles tissues. Based on the pathogenesis of asthmatic constriction, several therapeutic strategies for asthma may be developed, including inhibition of allegoric immunological response, attenuation of airway remodeling and relaxation of airway smooth muscle contraction.

Chronic obstructive pulmonary disease (COPD) includes a condition in which there is limited airflow in the lungs. COPD may develop and worsens over time, and result in changes in the small airways of a subject with COPD. These changes cause walls to narrow during expiration, making the subject hard to breathe out. In certain subjects, the small sacs where oxygen and carbon dioxide are exchanged are destroyed, gradually starving the body of oxygen. COPD may be associated with a set of breathing-related symptoms, for example, being out of breath, chronic cough, spitting or coughing mucus (phlegm), the ability to exhale (breathe out) getting worse over time. COPD may have three forms: emphysema, chronic bronchitis, and obstructive bronchiolitis. The emphysema may be marked by destruction of the alveoli, grape-like clusters of air sacs at the end of the smallest airways (the bronchioles) in the lung. The chronic bronchitis may be defined as coughing and overproduction of mucus for a threshold time during a predetermined time period. The obstructive bronchiolitis involve an inflammatory condition of the small airways. COPD may also be called as chronic obstructive airways disease, Chronic obstructive lung disease, Chronic bronchitis, Emphysema, Bronchitis-chronic. Smoking may cause COPD while other reasons may also lead to COPD. For example, a subject who lacks alpha-1 antitrypsin or is exposed to certain gases or fumes may develop COPD. One of the tests for COPD is a lung function test called spirometry, which involves blowing out as hard as possible into a small machine that tests lung capacity. In some instances, using a stethoscope to listen to lungs, pictures of lungs, blood tests may be used for determination of COPD.

Smooth muscle contractility may be regulated by a network of signaling pathways centered on the molecular motor myosin as well as membrane properties associated with calcium handling and cell adhesion. Depolarization of the cell membrane activates voltage-gated $Ca^{2+}$ channels, resulting in $Ca^{2+}$ influx and activation of myosin cross-bridge cycling on actin filaments by regulatory light chain (RLC) phosphorylation catalyzed by $Ca^{2+}$/calmodulin-dependent myosin light chain kinase (MLCK). Agonist stimulation of G protein-coupled receptors on smooth muscle cell surfaces may recruit other regulatory elements, thereby regulating contractility through a calcium sensitization mechanism. Smooth muscle contractility may be mediated through a calcium-dependent mechanism. The use of MLCK knockout mice shows that myosin light chain kinase (MLCK) is required for smooth muscle contraction, emphasizing the importance of a calcium-dependent mechanism for smooth muscle contraction. Importantly, deletion of MLCK leads to an abolishment of asthmatic airway constriction.

The various embodiments described above may be combined to provide further embodiments. Aspects of the embodiments can be modified, if necessary to employ concepts of the various patents, applications and publications to provide yet further embodiments.

These and other changes may be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

*kudingcha* Extract (KE) Relaxed Evoked Force of Airway Smooth Muscle 1000 g dried leaves of *Ilex latifolia* Thunb were extracted by 90-100% alcohol overnight or longer, and then remove the alcohol. The resultant pellet was dissolved in distilled water followed by ethyl acetate and n-butanol sequential extraction. The substances in ethyl acetate (EtOAc phase), n-butanol (n-BuOH phase) and water (water phase) were pelleted by dry out the solvents. The extracts from different phases were dissolved in ethanol and subjected to analyzing activity towards relaxation of airway smooth muscles. The leaves of *kudingcha* were purchased from the Huilong pharmaceutical company, and identified by Professor Pan Yang at Nanjing University of Chinese Medicine, P. R. China.

Briefly, the entire respiratory tree was rapidly removed and immersed in Krebs-Henseleit buffer (118.1 mM NaCl, 4.7 mM KCl, 1.2 mM $MgSO_4$, 2.5 mM $CaCl_2$, 1.0 mM $NaH_2PO_4$, 25 mM $NaHCO_3$ and 11.1 mM glucose, pH 7.4). Bronchial rings, 2 mm in length, were isolated from pulmonary bronchi using a dissection microscope. Then the bronchial segments were mounted in a small-vessel wire myograph chamber (Danish Myo Technology, Aarhus, Denmark) by threading on two steel wires (40 µm in diameter) secured to two supports. One support was attached to a force transducer for measurements of isometric force development, and the other was attached to a micrometer controlling ring circumference. The preparation was kept in the chamber, immersed in 5 ml of Krebs-Henseleit solution, bubbled with 5% $CO_2$ and 95% $O_2$ and maintained at 37° C. The initial isometric tension of bronchial ring was set to 0 mN prior to equilibration for 20 min. The bronchial ring was then stretched in order to keep the force at 5 mN followed by an additional equilibration for 20 min. The isometric forces produced by bronchial ring was recorded with a data acquisition and analysis program (Danish Myo Technology, Aarhus, Denmark).

Figure 1D:
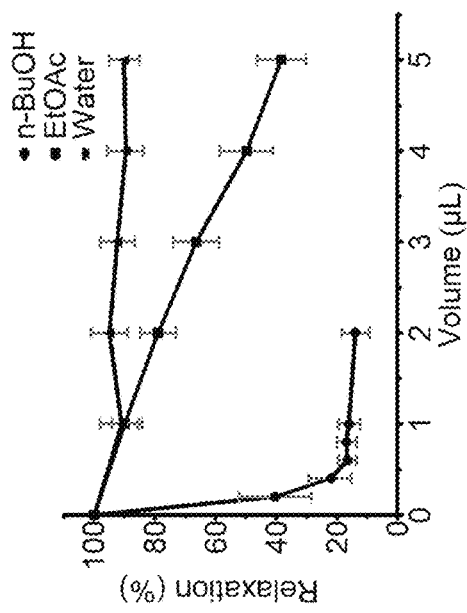
Figure 1B:
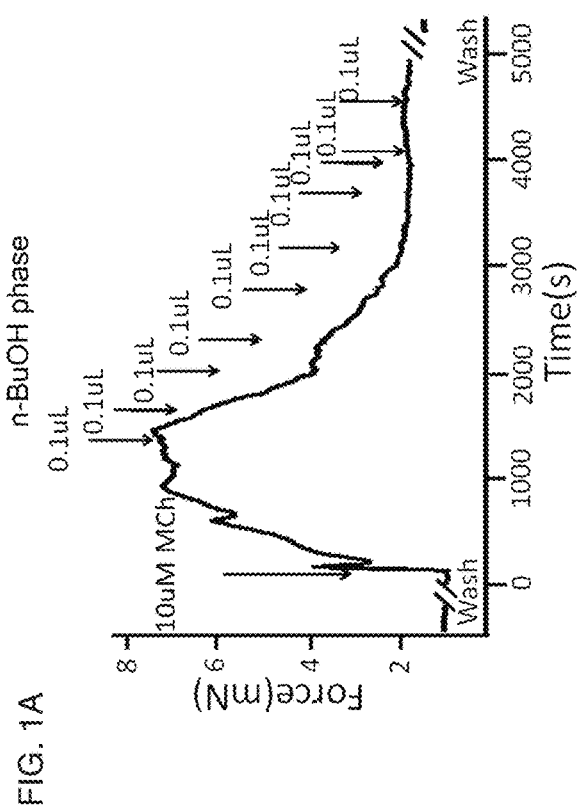
Figure 1C:
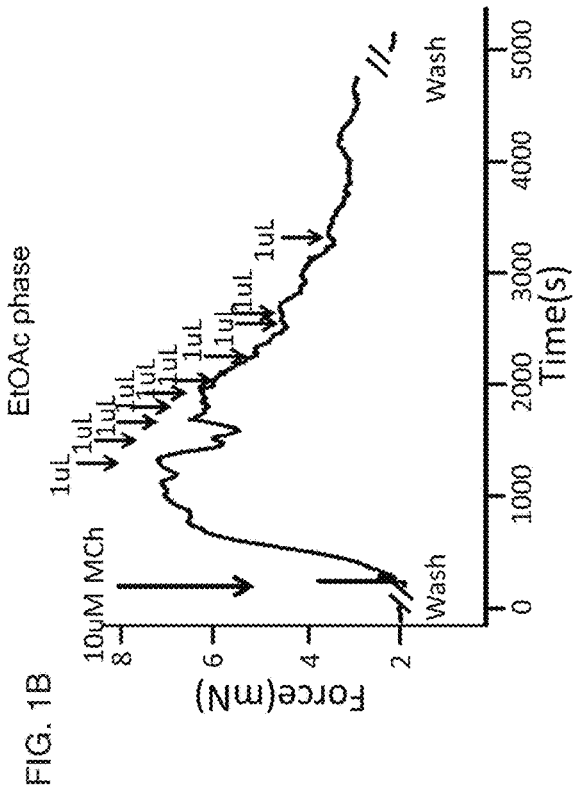

The robust relaxation effect and low risk of toxicity of KE on airway smooth muscle indicates its promising prospects for development. To identify the active ingredients of KE, the KE was divided into three parts including EtOAc phase, n-BuOH phase and water phase using EtOAc and n-BuOH sequential extraction. Upon the airway smooth muscle rings reached a relative steady contraction state evoked by MCh, accumulated volume of these three phases was added to assess the relaxation capacity. As the dose increased, all these three parts can relax the bronchial rings with a dose dependent manner, but showed considerable differences in efficiency (FIGS. 1 A, B, C). Surprisingly, the bronchial rings started relax as little as 0.1 µL of n-BuOH phase added, and 1 µL nearly completely relaxed the contractile bronchial rings (FIGS. 1 A, D). On the other hand, 1 µL of EtOAc phase just relaxed the rings to 90%. And 5 µL of extract from water phase almost had no relaxation activity (FIG. 1D). The results suggest that n-BuOH phase is more active than other parts of KE on relaxing airway smooth muscle. These results demonstrate that KE extracts efficiently relax evoked force of airway smooth muscle.

Example 2

*kudingcha* Extract (KE) Inhibits Asthmatic Airway Constriction

Asthmatic airway constriction may be attributable to hyperresponsive smooth muscle and tissue remodeling. To test the effect of KE on release of the constriction, an asthma animal model was established through which evaluated the efficacy of KE extract from n-butanolphase.

Asthma mice were established as reported previously. Briefly, six to eight-week-old female C57BL/6 mice were carried out by intraperitoneal injection of 100 µg ovalbumin and 4 mg Imject Alum (ThermoFisher Scientific) in total volume of 0.2 mL on days 0 and 14. These mice were then challenged with 1.5%-2% aerosolized ovalbumin for 1 h on days 24, 25 and 26. The efficacy of drugs was evaluated by measuring airway resistance in these mice 24 h after the last challenge.

The airway resistance was measured through an invasive method as described in previous reports. In brief, the mice were anesthetized with 240 mg/kg Avertin and the trachea was cannulated with an 18-gauge metal needle. Mechanical ventilation (FlexiVent; SCIREQ Inc., Montreal, Canada) was applied at a frequency of 150 breaths per minute, a tidal volume of 10 ml/kg, and positive end-expiratory pressure of 2.5 cm $H_2O$. Prior to methacholine challenge, deep inflation was applied followed by administration of aerosolized PBS to obtain stabilization of airway resistance (Rrs, $cmH_2O·s/mL$). The Rrs after PBS was considered to be the baseline.

Then mice were challenged with sequential concentrations of methacholine with a dose of 2.0, 4.0, 8.0, 16, 32 and 64 mg/mL by an ultrasonic nebulizer until reaching bronchoconstrictive phase that was four to five folds greater than baseline. Three minutes after the last dose of methacholine inhalation, the reagents were delivered by the same ultrasonic nebulizer. The Rrs measurements were performed every 30 s throughout the experiments. The negative control for these studies was PBS, because all the solvents for reagents used here were PBS. As a positive control, albuterol (3 µg; Sigma), the most widely used β-agonist as an effective bronchodilator for asthma therapy, was used.

Figure 2A:
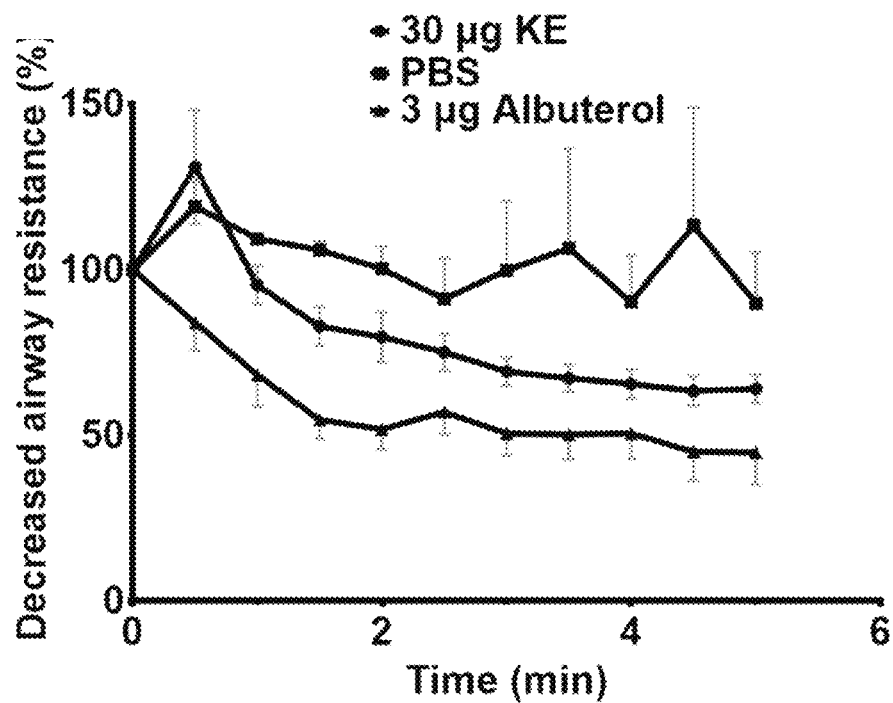
FIGS. 2A-B illustrates that n-BuOH phase of *kudingcha* extracts releases asthmatic airway resistance in mice. C57BL/6 adult mice were induced with OVA and challenged with methacholine.
Figure 2B:
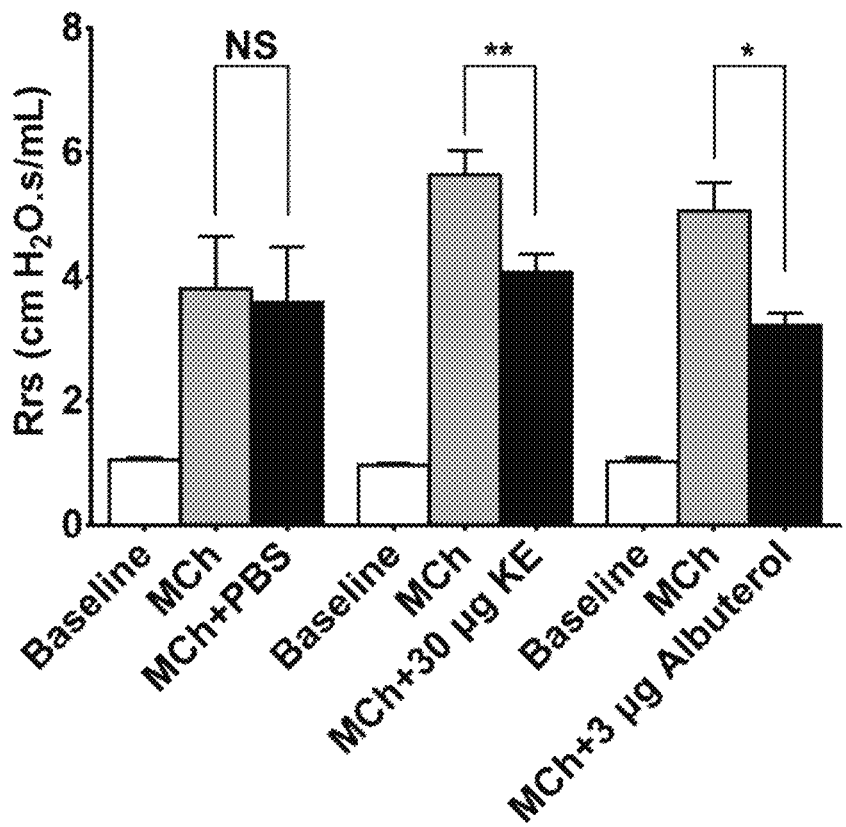

After challenge with MCh, the mice displayed sustained airway constriction. Upon treatment with 30 µg n-BuOH phase, the airway resistance declined immediately within 1 minutes followed by gradual reduction. As a positive control, albuterol (3 µg) also led to significant reduction of airway resistance in a similar manner (FIGS. 2A and B). These results show that n-BuOH phase efficiently releases asthmatic airway resistance Example 3

Identification of Active Ingredients from n-BuOH Phase

For column chromatography, silica gel (Qingdao Marine Chemical Industry, 100-200 mesh) and silica gel for thin-layer chromatography (Qingdao Marine Chemical Industry, H degree) were used. Homogeneity of fractions was determined on Thin layer Chromatography (TLC) with silica gel F, which was coated on glass plates (Qingdao Marine Chemical Industry). The spots were detected by spraying with 10% $H_2SO_4$ EtOH reagent followed by 105° C. heating for 5 min. Reddish-purple spots will appeared at the area containing substances.

100 mL KE extracted with EtOAc (5×100 mL) and n-BuOH (5×100 mL) successively. The n-BuOH layer were combined and concentrated to dryness in vacuo. Then the residue was powdered (27.41 g in all) and subjected (12 g) to column chromatography (CC) on silica gel (mixture of 540 g 100-200 mesh silica gel and 180 g H degree silica gel) using a stepwise gradient elution of $CHCl_3$-MeOH (100:0, 3.5 L), (98:2, 3 L), (95:5, 5.5 L), (90:10, 33.5 L), (85:15, 20 L), (80:20, 24.5 L). Eventually, 27 fractions (Fr. 1-Fr. 27) were obtained after Homogeneity.

Figure 3A:
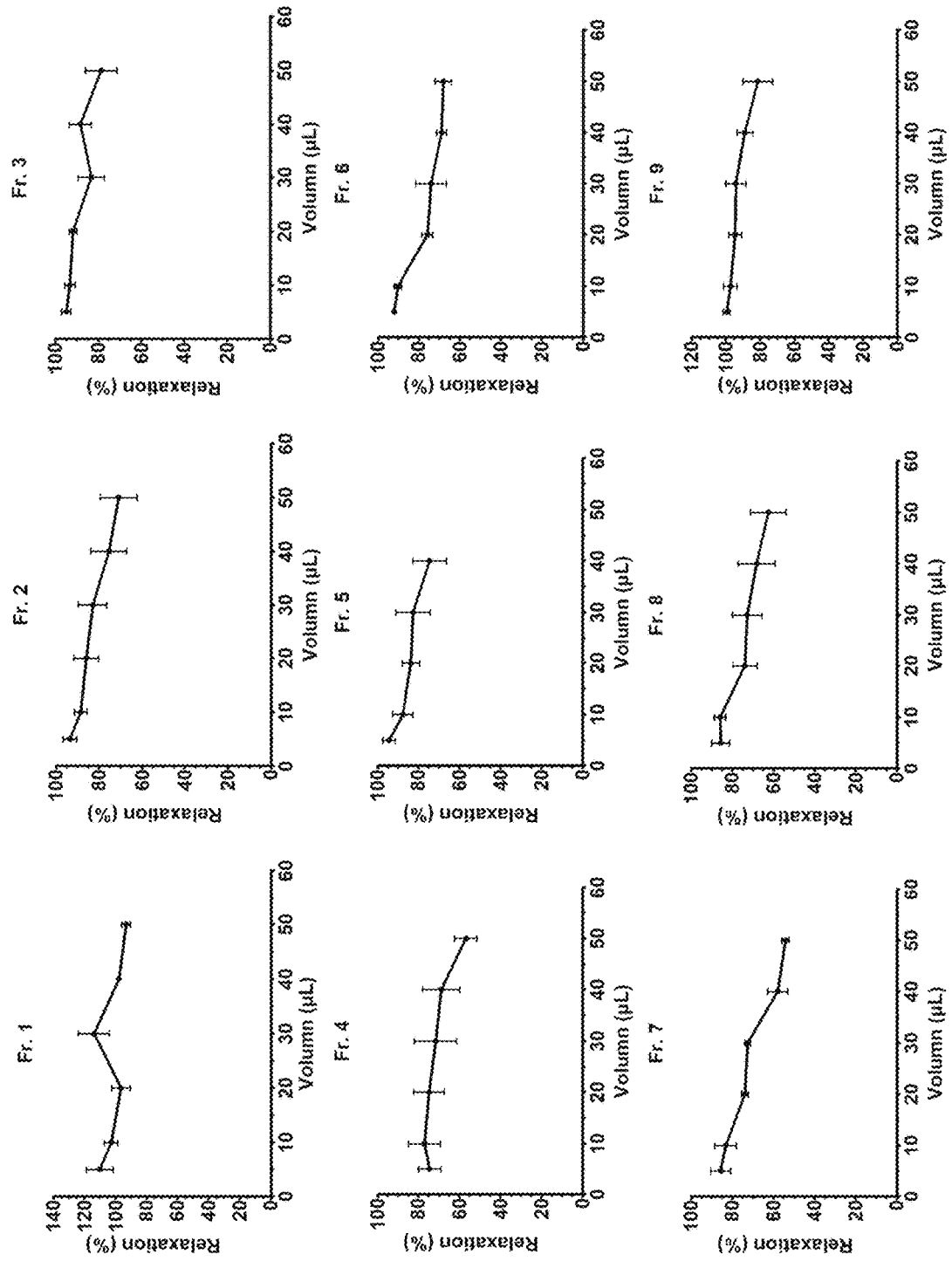
FIGS. 3A-C illustrate partial purification for active ingredients of *kudingcha* (Fr=the collected fraction after elution).
Figure 3B:
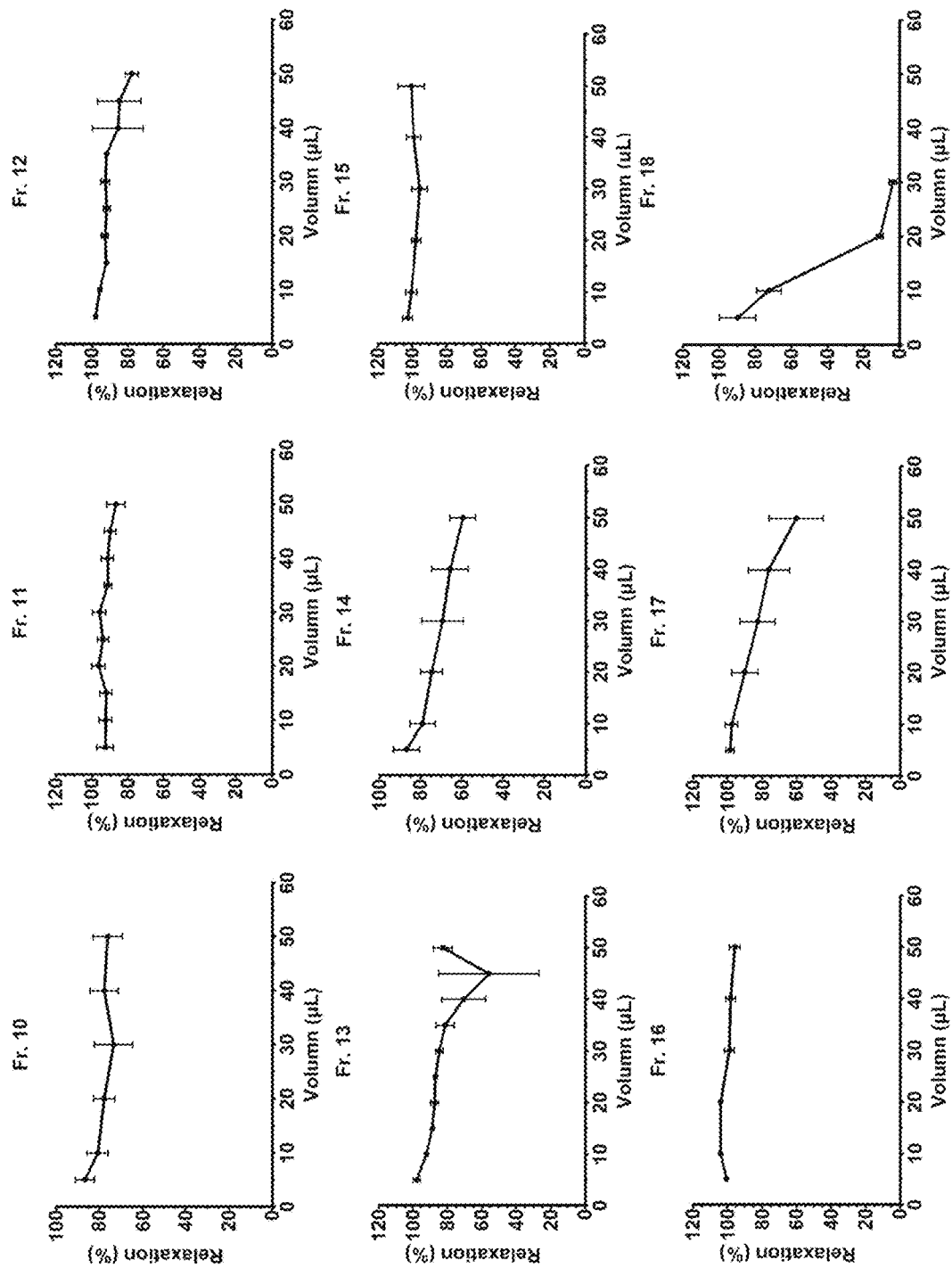
Figure 3C:
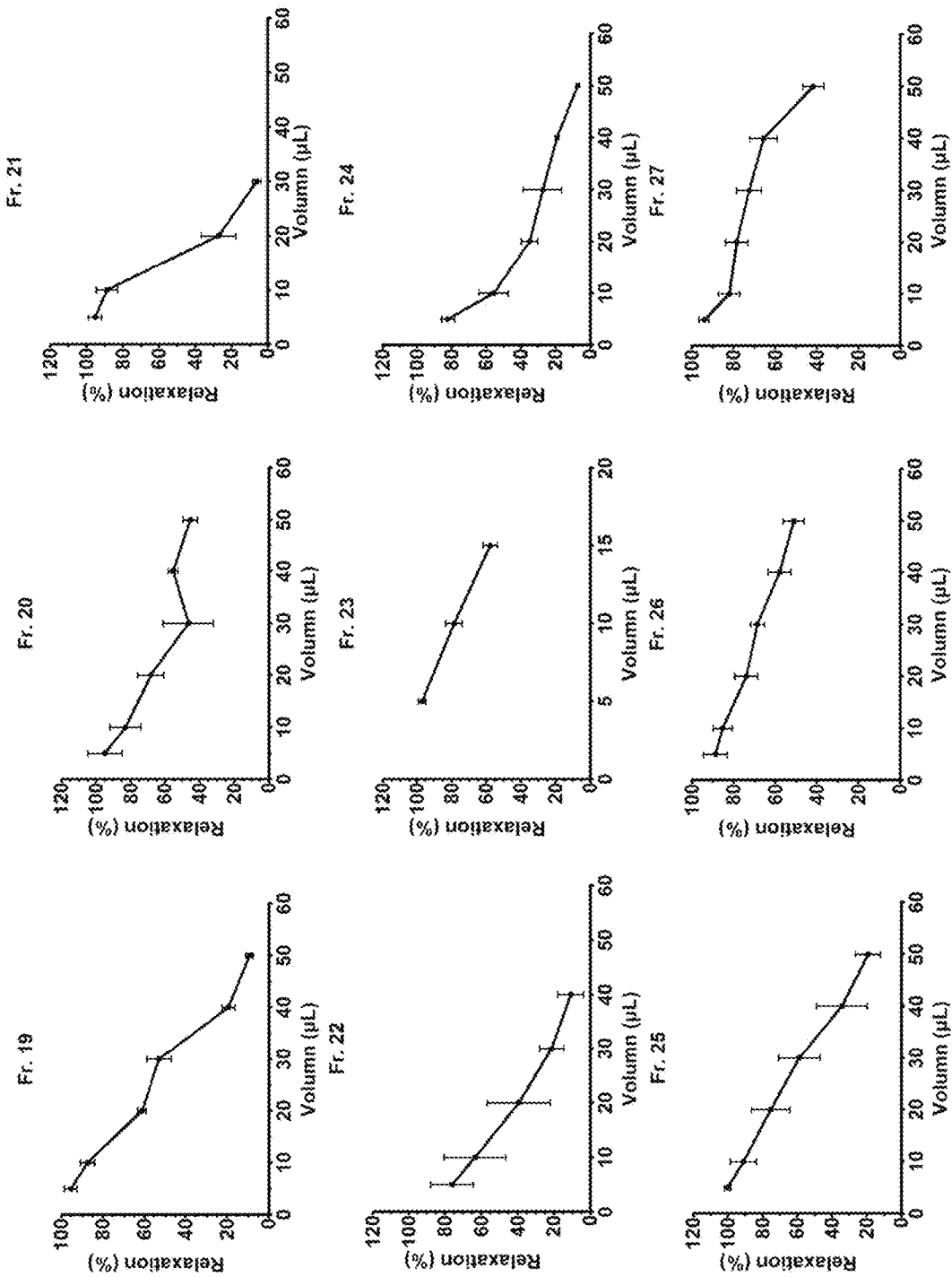
Figure 4A:
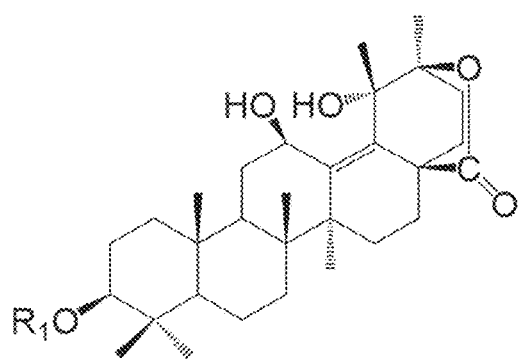
FIGS. 4A-F illustrate structures of partial identified compounds in *kudingcha*.
Figure 4A:
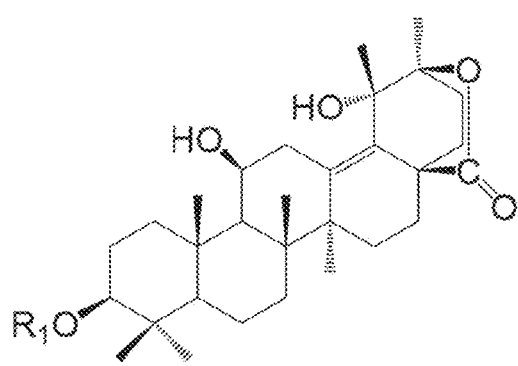
Figure 4A:
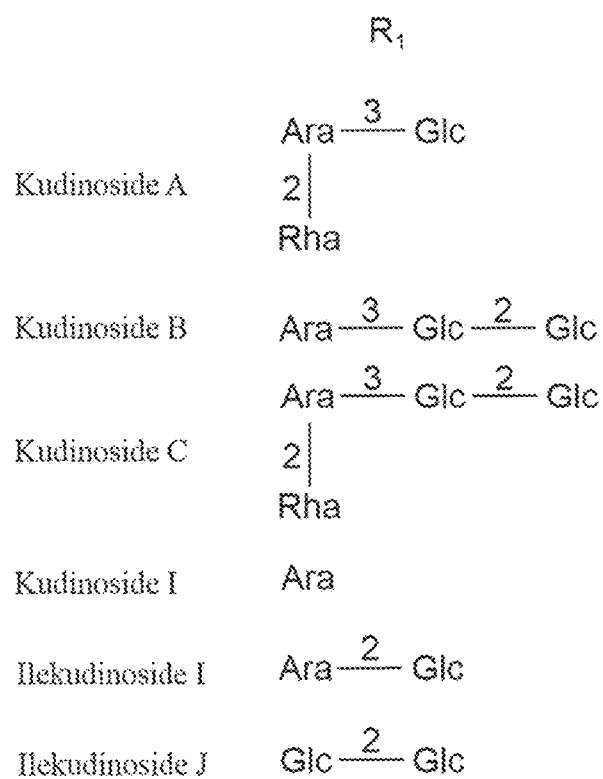
Figure 4A:
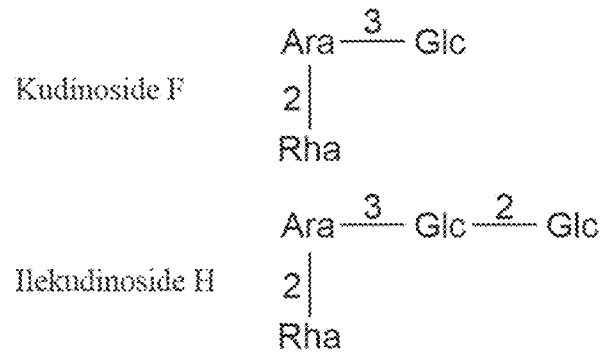
Figure 4B:
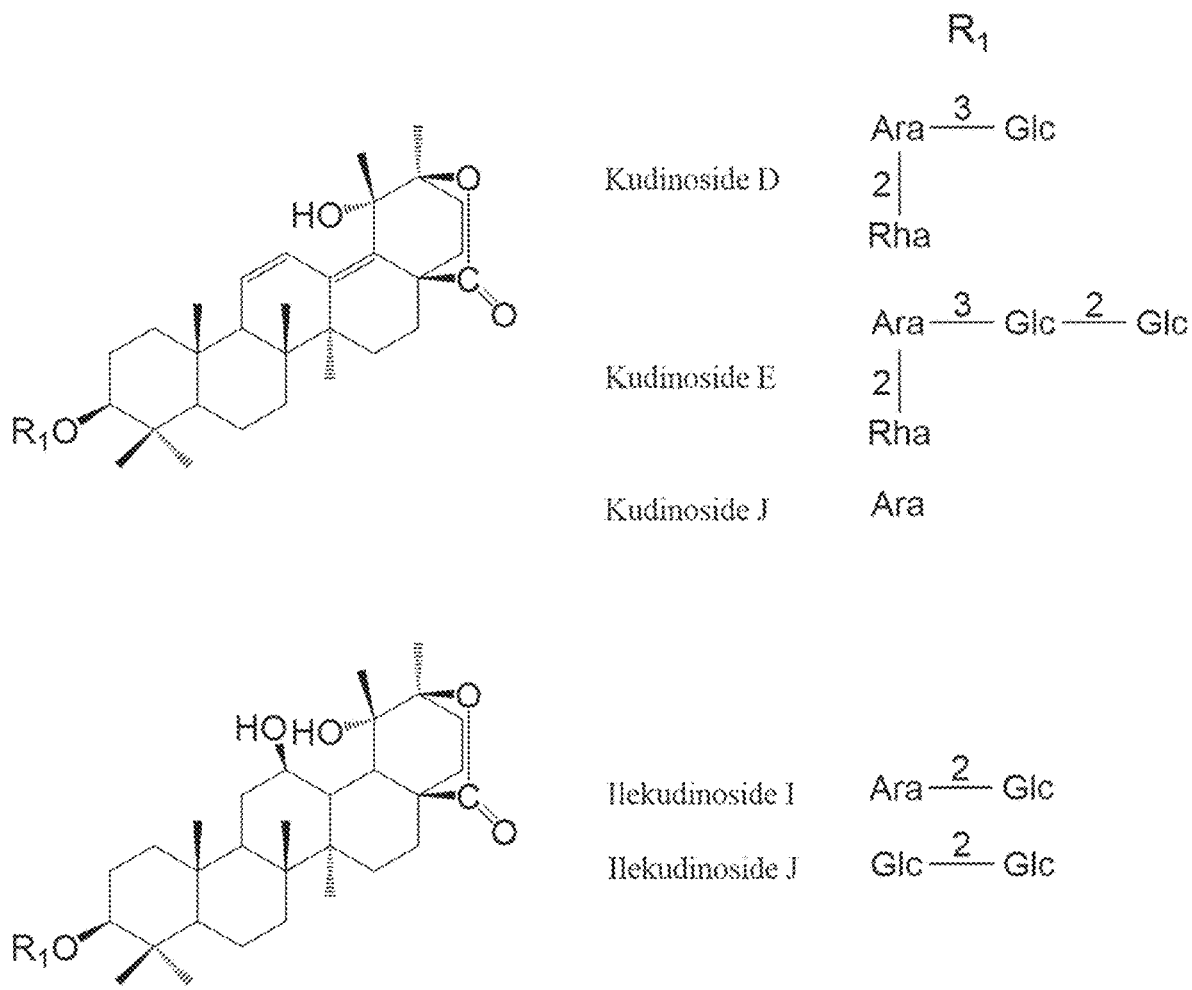
Figure 4C:
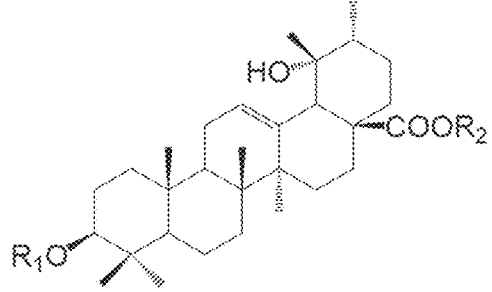
Figure 4C:
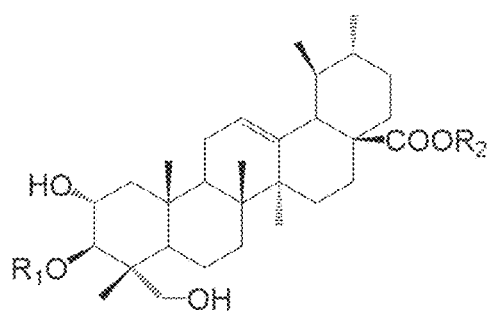
Figure 4D:
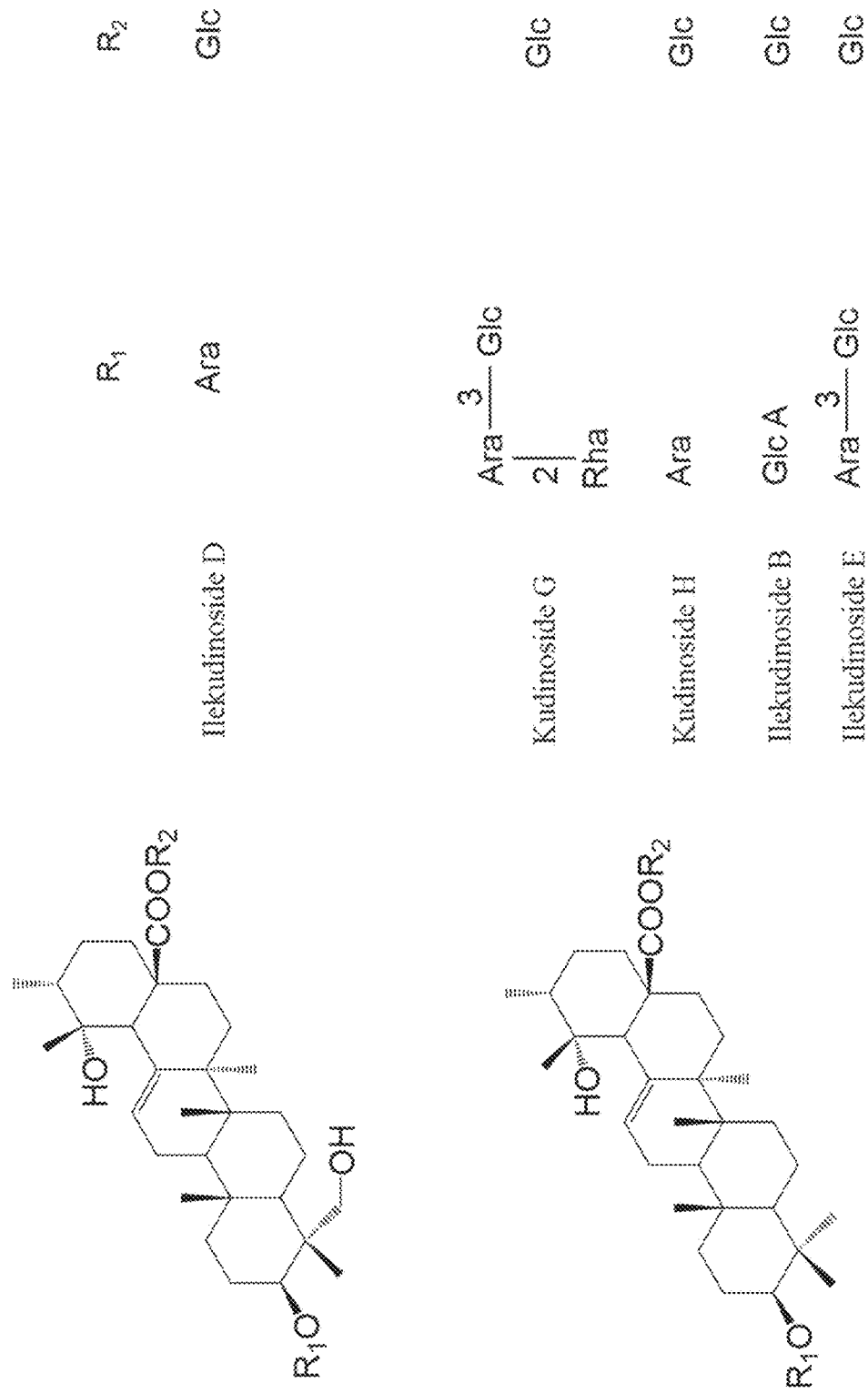
Figure 4E:
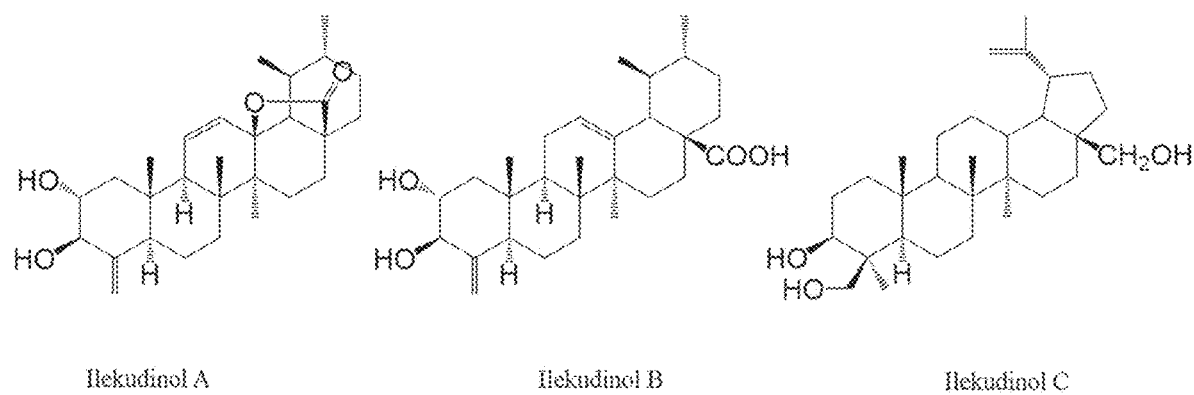
Figure 4F:
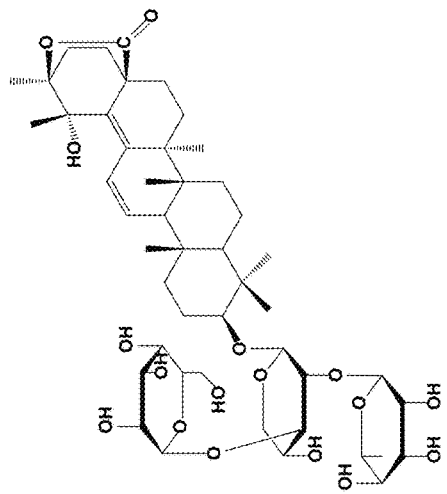
Figure 4F:
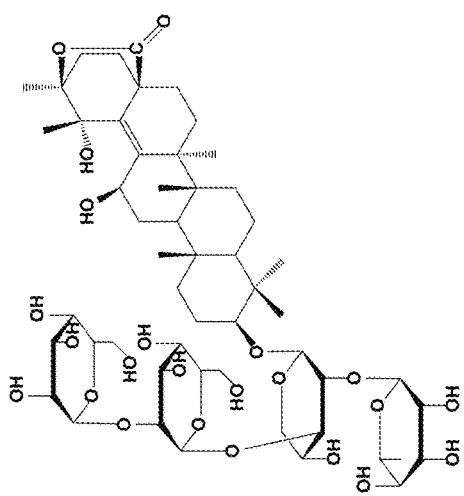
Figure 4F:
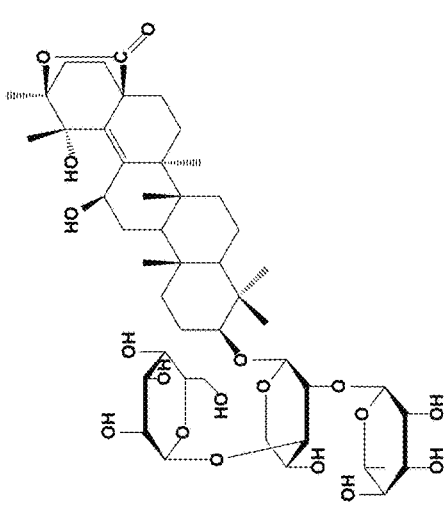
Figure 4F:
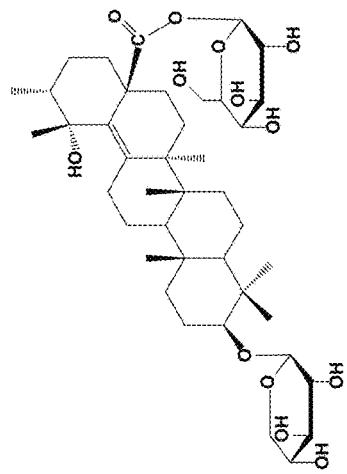
Figure 4F:
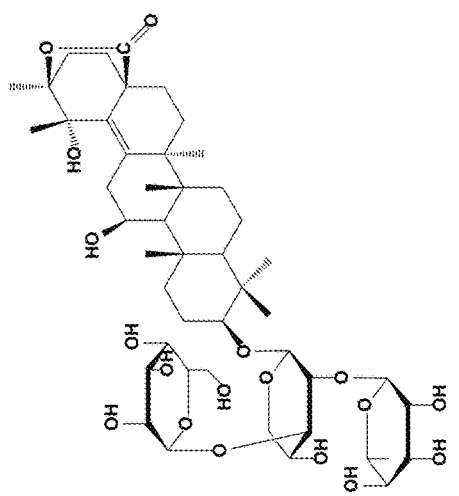

As n-BuOH phase is still a crude extraction part, it is necessary to identify the compound(s) with strong activity toward airway smooth muscle relaxation. N-BuOH phase was extracted by column chromatography and separated it into 27 fractions. For each individual fraction, the similar strategy was used to address the relaxation effect on bronchial rings in vitro. The former 17 fractions exhibited little effect on reducing the force even by adding 50 µL into the chamber. Strikingly, the 18th fraction (Fr. 18) showed profound effect on relaxing bronchial rings. Upon addition with 20 µL of Fr. 18 extract almost decreased the evoked force completely. Fr. 19 to Fr. 25 also had strong efficacy of relaxing, but was weaker than Fr. 18. The extracts from Fr. 26 and Fr. 27 showed much less active to relax the rings (FIGS. 3A-C). Throughout the whole fractions screening, it is concluded that the putative compound(s) might be enriched in Fr. 18 to Fr. 25. These results show that the extract in Fr. 18 is more efficient than other ingredients with relaxation effect, and relaxes the bronchial rings in a dose responsive manner.

Example 4

Structural Identification and Functional Characterization for the Active Compounds of kudingcha To investigate identity of the active compounds, the substances in fraction 18 was purified with HPLC, and then analyzed their individual structures with NMR and others tools. In particular embodiments, the extracts were generated from Ilex latifolia Thunb and Ilex kudingcha C. J. Tseng.

The partial purified extract was further purified on preparative HPLC using MeOH—$H_2O$ as a flow. Each absorption peak was collected and subjected to spectra analysis.

NMR spectra, including $^1H$ NMR, $^{13}C$ NMR, $^1H$-$^1H$ COSY, DEPT, HMBC and HSQC, were obtained in pyridine $d_5$ using a 500 MHz instruments. Preparative high performance liquid chromatography (HPLC) was carried out using a system composed of a Waters 2545 binary gradient module, a Waters 2489 UV/Visible detector, a Waters 2767 sample manager and a XBridge™ Prep C18 5 µm OBD™ Column (19×150 mm, detected at 260 nm).

After purification with HPLC, a series of compounds were obtained from the extracts. NMR spectra results indicated that these compounds are related to triterpenoid saponins including Kudinosides and Ilekudinosides. Table 1 shows an example of NMR spectra data and molecular structures of two active compounds which is similar to kudinoside A and kudinoside D. Characterization of structure of the active compounds was summarized in FIGS. 4A-F.

Kudinosides significantly relaxed the bronchial rings in a dose-dependent manner. Kudinoside D and A show highly effective among the triterpenoid saponins. Their dose-responsive effect on relaxation of airway smooth muscle was measured. When the force evoked by acetylcholine reached a relatively steady state, kudinosides were added to the bath in cumulative concentrations (0.1 µM, 0.3 µM, 1 µM, 3 µM, 10 µM, 30 µM). Both kudinoside D and kudinoside A significantly relaxed bronchial rings in a dose-dependent manner (FIGS. 5A-B). When the concentration of kudinoside D increased to 10 µM, about 50% of the force was relaxed. Strikingly, upon treatment with 30 µM of kudinoside D, more than 80% of the force was relaxed (FIG. 5B). Similarly, 30 µM of kudinoside A also led to 80% inhibition of evoked force. Note that the relaxation effect of kudinosides was completely reversible, because the relaxed muscles restored response to MCh after washing off.

Various triterpenoid substances were identified (e.g., FIGS. 4A-F) from Ilex latifolia Thunb and Ilex kudingcha C. J. Tseng, and characterized preliminarily the association of structure and biological activity. As illustrated in FIGS. 4A-F, the basic structure of pentacyclic triterpenoids is included, and side modification (e.g., the existence of lactone moiety) may affect biological activity. For example, Kudinoside H fails to show effective bronchial ring relaxation.

TABLE 1

$^{13}$C NMR spectral data for Kudinoside A (1), C (2), D (3) and F (4) in Pyridine-$d_5$ (125 MHz)

| | Aglycone Part | | | | | Carbohydrate Moieties | | | |
|---|---|---|---|---|---|---|---|---|---|
| | $\delta_c$ | | | | | $\delta_c$ | | | |
| Position | 1 | 2 | 3 | 4 | Position | 1 | 2 | 3 | 4 |
| 1 | 39.193 | 39.219 | 38.464 | 39.109 | 3-Ara 1 | 104.742 | 105.097 | 104.75 | 104.803 |
| 2 | 26.234 | 26.25 | 26.468 | 26.662 | 2 | 74.717 | 74.393 | 74.862 | 74.746 |
| 3 | 88.269 | 88.436 | 88.209 | 88.08 | 3 | 82.143 | 82.835 | 82.145 | 82.197 |
| 4 | 39.624 | 39.578 | 39.694 | 39.571 | 4 | 68.198 | 69.421 | 68.198 | 68.232 |
| 5 | 56.233 | 56.382 | 55.404 | 55.928 | 5 | 64.833 | 65.748 | 64.838 | 64.88 |
| 6 | 18.514 | 18.559 | 18.391 | 18.444 | Glc 1 | 104.669 | 103.038 | 104.807 | 104.755 |
| 7 | 35.485 | 35.491 | 32.973 | 35.189 | 2 | 74.597 | 84.628 | 74.987 | 74.97 |
| 8 | 41.697 | 41.718 | 42.222 | 42.825 | 3 | 78.223 | 78.422 | 78.296 | 78.618 |
| 9 | 44.902 | 44.895 | 54.574 | 50.164 | 4 | 71.437 | 70.873 | 71.554 | 71.51 |
| 10 | 36.985 | 37.001 | 36.674 | 37.151 | 5 | 78.557 | 78.353 | 78.611 | 78.287 |
| 11 | 28.834 | 28.852 | 127.224 | 71.51 | 6 | 62.528 | 62.396 | 62.632 | 62.597 |
| 12 | 66.06 | 66.075 | 128.429 | 33.521 | Glc 1 | | 106.331 | | |
| 13 | 146.366 | 146.391 | 140.757 | 143.529 | 2 | | 76.117 | | |
| 14 | 43.894 | 43.911 | 42.249 | 45.545 | 3 | | 78.19 | | |
| 15 | 28.834 | 28.852 | 25.893 | 29.279 | 4 | | 70.504 | | |
| 16 | 26.69 | 26.773 | 26.351 | 26.963 | 5 | | 78.808 | | |
| 17 | 44.067 | 44.089 | 43.847 | 46.236 | 6 | | 61.893 | | |
| 18 | 137.477 | 137.459 | 135.051 | 135.742 | Rha 1 | 101.913 | 100.999 | 101.981 | 101.958 |
| 19 | 74.308 | 74.313 | 74.185 | 73.276 | 2 | 72.424 | 72.38 | 72.464 | 72.47 |
| 20 | 85.646 | 85.674 | 85.908 | 85.332 | 3 | 72.523 | 72.507 | 72.582 | 72.563 |
| 21 | 28.366 | 28.38 | 28.597 | 29.221 | 4 | 73.924 | 73.968 | 73.979 | 73.947 |
| 22 | 32.826 | 32.831 | 32.973 | 32.505 | 5 | 70.018 | 69.791 | 70.075 | 70.039 |
| 23 | 28.04 | 28.111 | 27.797 | 28.019 | 6 | 18.171 | 18.285 | 18.489 | 18.601 |
| 24 | 16.946 | 17.115 | 16.451 | 17.131 | | | | | |
| 25 | 16.731 | 16.771 | 18.614 | 16.907 | | | | | |
| 26 | 18.581 | 18.173 | 16.54 | 16.812 | | | | | |
| 27 | 23.446 | 23.464 | 18.714 | 21.574 | | | | | |
| 28 | 175.37 | 175.403 | 175.179 | 175.339 | | | | | |
| 29 | 25.189 | 25.208 | 23.733 | 26.574 | | | | | |
| 30 | 19.457 | 19.472 | 19.518 | 20.186 | | | | | |

Figure 8A:
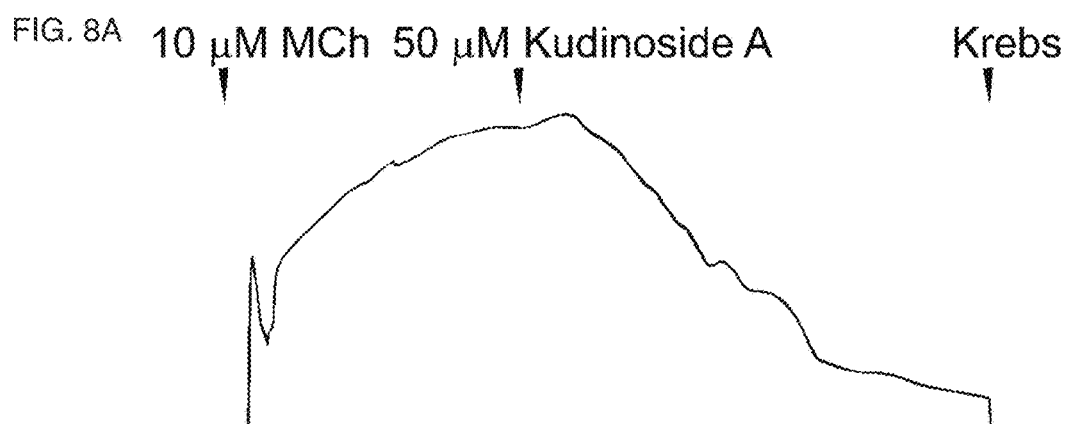
FIGS. 8A-C illustrate the relaxation of airway smooth muscle by Kudinoside A, the Organic Phase and the Water Phase after HCl treatment. After HCl treatment, the reaction system was divided into Organic Phase and Water Phase by extracted with $CH_3Cl$. Further, 5 µL of Organic Phase and Water Phase, as well as 5 µL of 50 mM Kudinoside A dissolved in DMSO were added in the chamber. The relaxation effect of these substances on 10 µM MCh-evoked contraction was measured.
Figure 8B:
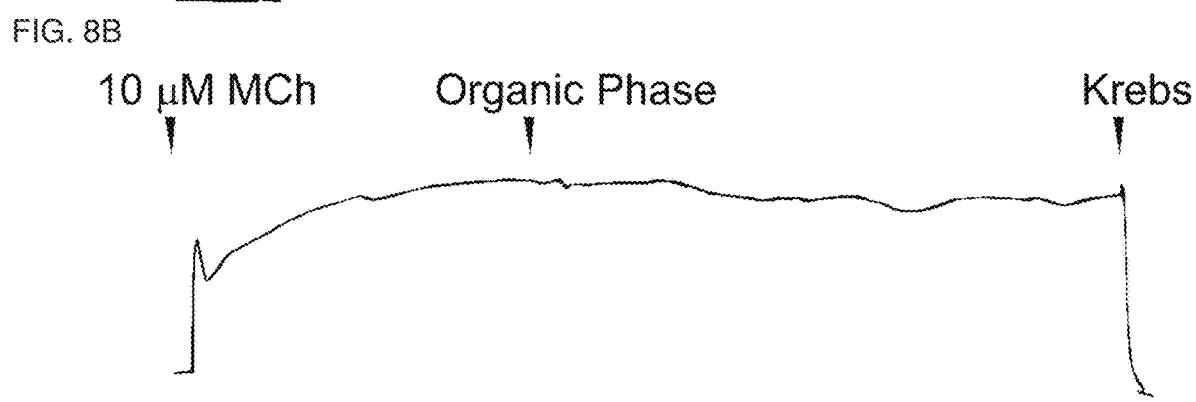
Figure 8C:
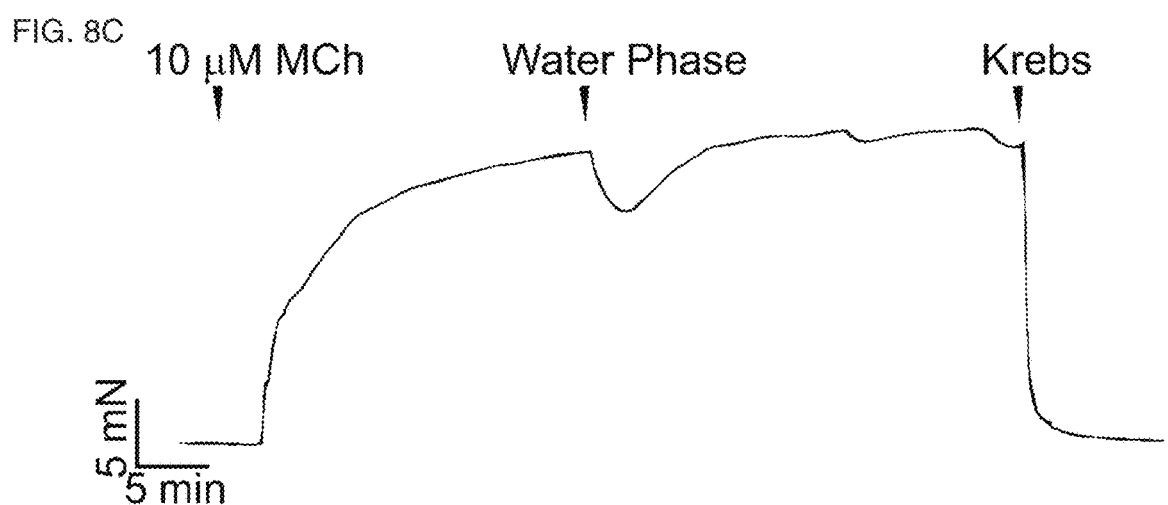

Since glycone and aglycone portions may be destroyed by hydrolysis of acid, certain kunidnosides were treated with 2 M HCl to remove the glycone residues. 1.9 mg Kudinoside A was immersed in 20 μL 2 M HCl followed by 95° C. boiling for 6 h, then diluted with ddH$_2$O and extracted with CH$_3$Cl. The organic and water layer were evaporated and dissolved in 20 μL DMSO. The resultant substances were subjected to relaxation assay. The aglycone portion is hydrophobic and is distributed in the organic phase. The sugars of glycone portion are hydrophilic, and glycone portion is dissolved in the water phase. As illustrated in FIGS. 8A-C, HCl treatment of Kudinosides leads to significant inhibition of relax activity since neither the substance in organic phase nor in water does phase relax the airway smooth muscle evoked by MCh stimulations. These results indicate that glycone may contribute to relaxant activities of certain Kudinosides.

In *Ilex latifolia* Thunb and *Ilex kudingcha* C. J. Tseng, the major aglycone of triterpenoid saponins including a C30 skeleton may contain a pentacyclic structure, as illustrated in FIGS. 4A-F. These aglycone of triterpenoid saponins may belong to ursane substitution patterns of pentacyclic triterpenoid saponins because they contain methyl residues both in C19 and C20. The basic aglycone skeleton of certain Kudinosides may contribute to relaxation activities of these Kudinosides. Further, failure of Kudinoside H to relax airway smooth muscle strips may indicate that the lactone moiety contributes to relaxation activities of certain Kudinosides. For example, pentacyclic triterpenoid saponins belong to a diverse group of triterpenoid saponins, and show various pharmacological activities. As a group of pentacyclic triterpenoid saponins, Kudinosides have relative less pharmacological activities and have a structure of lactone moiety.

To investigate the association of lactone structure with kudinosides activities, 45 kinds of well-documented pentacyclic triterpenoids were selected and subjected to relaxation assay. These pentacyclic triterpenoids include Glycyrrhetinic acid, Glycyrrhizic acid, 18-B-Glycyrrhetinic acid, Saikosaponin A, Saikosaponin B1, Sailosaponin B2, Saikosaponin C, Saikosaponin D, Raddeanin A, Phytolaccagenin, Esculentoside A, Bayogenin, α-Boswellic acid, Ginsenoside-Ro, Araloside X, Dipsacoside B, Akebia saponin D, Echinocystic acid, Hedera saponin B, Ciwujianoside B, Pedunculoside, Soyasaponin Ba, Soyasaponin Bb, Asiatic acid, Asiaticoside, Macranthoidin B, Momordin Ic, Demethylzeylasteral, Maslinic acid, Wilforlide A, Corosolic acid, Rotundic acid, Anemoside B4, Glycyrrhizic acid ammonium salt, Tenuifolin, Polygalacic acid, Polygalasaponin F, Madecassic acid, Madecassoside, Epifriedelanol, Sodium Aescinate, Hederagenin, α-Hederin, Hederacoside C, Hederacoside D. These pentacyclic triterpenoids are from different plants and have C30 aglycone skeleton; their modifications including hydroxylations and glycosidations are different. These substances have no intramolecular esterification modification. For example, some of substances are saponins, and others are sapogenins. These substances may be dissolved in DMSO with a concentration of 500 mM preparing for bronchi ring isometric assay. The results show that 5 out of 45 compounds that showed about 50% relaxation of MCh-evoked force at a final concentration of 500 μM. These five compounds contain Glycyrrhetinic acid, Saikosaponin C, Soyasaponin Bb, Raddeanin A and Phytolaccagenin. Among these five compounds, two compounds may relax more than 80% force. These two compounds contain Glycyrrhetinic acid and Saikosaponin C, and are able to relax airway smooth muscle in a dose dependent manner. However, their IC50 values (Glycyrrhetinic acid: 84.3 μM; Saikosaponin C: >150 μM) were higher than that of Kudinoside A and Kudinoside D. These results indicate that lactone moiety may contribute to relaxation activities of certain Kudinosides.

Lactones are cyclic esters formed by intracellular esterification of the corresponding hydroxycarboxylic acid. Like the straight-chained esters, the lactones may be hydrolyzed by incubating in a base solution, such as sodium hydroxide. The lactone moiety of Kudinosides is a δ-lactone ring with a configuration of the 20,28β-lactone. In order to disrupt the lactone moiety of Kudinosides, 5 mg Kudinoside A were dissolved it in 108 μL 0.9% NaCl solution followed by adjusting a pH to 9 with sodium hydroxide, and then incubated the reaction mixture with shaking at 37° C. for 6 h. As the hydrolysis-condensation reaction of the lactones is reversible, the resultant substance showed significantly reduced relaxation activity compared with native Kudinoside A. These results confirm that the lactone moiety contribute to the relaxation activity of certain Kudinosides.

Relaxation activities from *kudingcha*-associated plants were investigated. Table 2 illustrates indicate a range of degrees of relaxing activity from low (+) to high (+++++); "+/−" indicates that plant has relatively weak relaxing activity, while "—−" indicates that plant has no relaxing activity.

TABLE 2 relaxation activity from Kudingcha-associated plants

| Plants (Latin name) | Activity |
|---|---|
| Ilex cornuta Lindl. & Paxton | +++ |
| Mahonia bealei (Fort.) Carr. | — |
| Ilex latifolia Thunb. | +++++ |
| Ligustrum henryi Hemsl. | — |
| Ligustrum pricei Hayata | — |
| Ligustrum japonicum Thunb. Var. pubescens Koidz. | — |
| Ligustrum lucidum W. T. Aiton | — |
| Ligustrum purpurascens Y. C. Yang | +/− |
| Ligustrum robustum (Roxb.) Blume | — |
| Ilex rotunda Thunb. | +++++ |
| Ilex zhejiangensis C. J. Tseng | ++ |
| Ilex ficoidea Hemsl. var. parvifilia S. H. Fu var. nov. ined. | +++++ |
| Ilex chinese Sims | +++ |
| Ilex macrocarpa Oliv. | ++ |
| Ilex pubescens Hook. & Arn. | ++++ |
| Ilex kudingcha C. J. Tseng | +++++ |

Example 5

The Effect of Kudinosides on Releasing Asthmatic Constriction in Animal

Acute asthma model mice were established as reported previously. Briefly, six to eight-week-old female C57BL/6 mice were carried out by intraperitoneal injection of 100 μg ovalbumin and 4 mg Imject Alum (ThermoFisher Scientific) in total volume of 0.2 mL on days 0 and 14. These mice were then challenged with 1.5%-2% aerosolized ovalbumin for 1 h on days 24, 25 and 26. The efficacy of drugs by measuring airway resistance in these mice 24 h was evaluated after the last challenge. The airway resistance was measured through an invasive method as described in previous reports. In brief, the mice were anesthetized with 240 mg/kg Avertin and the trachea was cannulated with an 18-gauge metal needle. Mechanical ventilation (FlexiVent; SCIREQ Inc., Montreal, Canada) was applied at a frequency of 150 breaths per minute, a tidal volume of 10 ml/kg, and positive end-expiratory pressure of 2.5 cm $H_2O$. Prior to methacholine challenge, deep inflation was applied followed by administration of aerosolized PBS to obtain stabilization of airway resistance (Rrs, $cmH_2O·s/mL$). The Rrs after PBS was considered to be the baseline. Then mice were challenged with sequential concentrations of methacholine with a dose of 2.0, 4.0, 8.0, 16, 32 and 64 mg/mL by an ultrasonic nebulizer until reaching bronchoconstrictive phase that was four to five folds greater than baseline. Three minutes after the last dose of methacholine inhalation, the reagents were delivered by the same ultrasonic nebulizer. The Rrs measurements were performed every 30 s throughout the experiments. The negative control for these studies was PBS, because all the solvents for reagents used here were PBS. As a positive control, albuterol (3 μg; Sigma), the most widely used β-agonist as an effective bronchodilator for asthma therapy, was used.

Figure 6A:
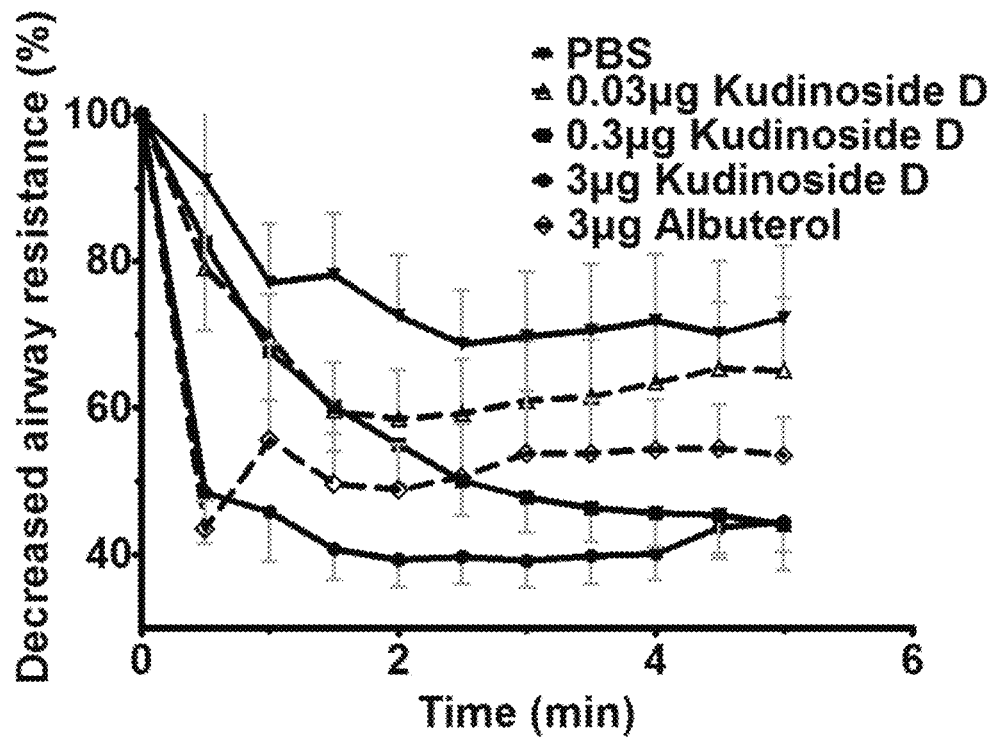
FIGS. 6A-B illustrate that Kudinoside D attenuates the airway resistance in acute asthma mouse model.
Figure 6B:
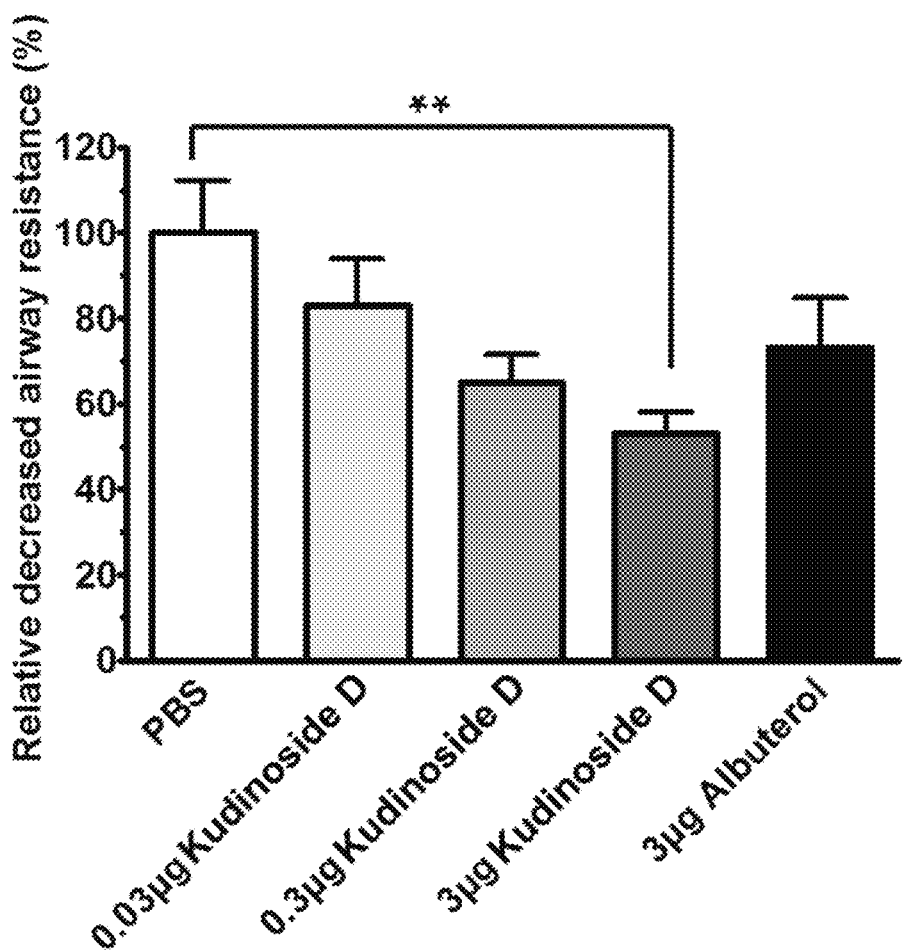

In PBS control, the airway resistance may reduce about 30% within 1-2 minutes given PBS by inhalation in bronchoconstrictive phase, the airway resistance reduced after inhalation, and then reached a steady state. Application of bronchodilators will cause the steady state to move downwards, indicating a decrease in airway resistance. After inhalation of kudinoside D, the airway resistance was reduced in a dose-dependent manner. 0.03 μg of kudinoside D caused a slight reduction while 0.3 μg or 3 μg led to a significant reduction of airway resistance as shown in FIG. 6A. At 1 minute after inhalation, 0.03 μg, 0.3 μg and 3 μg of kudinoside D reduced airway resistance to 69.65±5.87%, 67.79±6.77% and 45.81±6.87% respectively, whereas 3 μg of albuterol led to a reduction of 55.59±13.07%. Surprisingly, at 3 minutes after inhalation, both 0.3 μg and 3 μg kudinoside D showed more reduction of airway resistance than that of 3 μg of albuterol. The dose-responsive effect of kudinoside D is shown in FIG. 6B. These results indicate that kudinoside D is a strong bronchodilator, even much stronger than albuterol.

To test immunological alteration of the asthmatic animals received treatment, histology analysis of the lung were conducted. Both groups of mice received either vehicle or kudinoside D showed comparable histological alterations including hemorrhage, inflammatory infiltrations of neutrophils and esiophilic cells etc. These results show that inhibition effect by kudinoside D was not contributed to failure of asthma model establishment.

The therapeutic efficacy of kudinoside C was measured and showed strong relaxation effect on airway smooth muscles. It also showed significant inhibition of airway constriction and its IC50 value was 150 μg. Kudinoside H, exhibited little effect on relaxation in vitro, had little inhibition activity of airway constriction in vivo, either. These results indicate that other kudinosides with relaxation activity in vitro may have inhibition effect on airway constriction in vivo and vice versa.

Example 6

Kudinosides Relax Airway Smooth Muscle Through Modulation of Calcium Influx

Calcium image (1-3): $Ca^{2+}$ signal was measured by recording 488 nm laser excited Fluo-4 fluorescence with a laser confocal microscope (FV-1000, Olympus). After 3 times washing with D-Hanks solution, primary cultured airway smooth muscle cells were loaded with 2.5 µM Fluo-4 AM and 0.02% pluronic acid (F127) in D-Hanks for 30 min at room temperature. Then washed 3 times with D-Hanks, incubated in H-T buffer at 37° C. for 40 min. $Ca^{2+}$ signal was measured by recording 488 nm laser excited Fluo-4 fluorescence with a laser confocal microscope (FV-1000, Olympus).

To assess the requirement of calcium reduction for kudinoside-mediated relaxation, smooth muscle tissues permeable were made. Briefly, the fresh bronchial ring were separated by sharp dissection from C57BL/6J mice. Following incubation for 10 minutes in H-T buffer, the muscle strips were treated for 5 minutes in $Ca^{2+}$-free H-T buffer and for 5 minutes in buffer A (30 mmol/L TES, 0.5 mmol/L dithiothreitol, 50 mmol/L KCl, 5 mmol/L $K_2EGTA$, 150 mmol/L sucrose, pH 7.4), and then were subsequently permeabilized in α-toxin (16,000 units/mL; Sigma) in buffer A for 40 minutes at room temperature.

Treatment with 10 mmol/L ionomycin (Sigma) in buffer A for 10 minutes was used to deplete $Ca^{2+}$ stores. Permeable tissues were washed in pCa 9.0 solution (20 mmol/L TES, 4 mmol/L $K_2EGTA$, 5.83 mmol/L $MgCl_2$, 7.56 mmol/L potassium propionate, 3.9 mmol/L $Na_2ATP$, 0.5 mmol/L dithioerythritol, 16.2 mmol/L phosphocreatine, 15 U/mL creatine kinase, pH 6.9), followed by incubation in pCa 4.5 solution (20 mmol/L TES, 4 mmol/L CaEGTA, 5.66 mmol/L $MgCl_2$, 7.53 mmol/L potassium propionate, 3.9 mmol/L $Na_2ATP$, 0.5 mmol/L dithioerythritol, 16.2 mmol/L phosphocreatine, 15 U/mL creatine kinase, pH 6.9) to elicit a sustained $Ca^{2+}$-induced contraction. After wash out the solution, permeable muscle strips were then incubated with pCa 5.0 solution and relaxed by adding Kudinoside D dissolved in pCa 5.0 solution.

Figure 7:
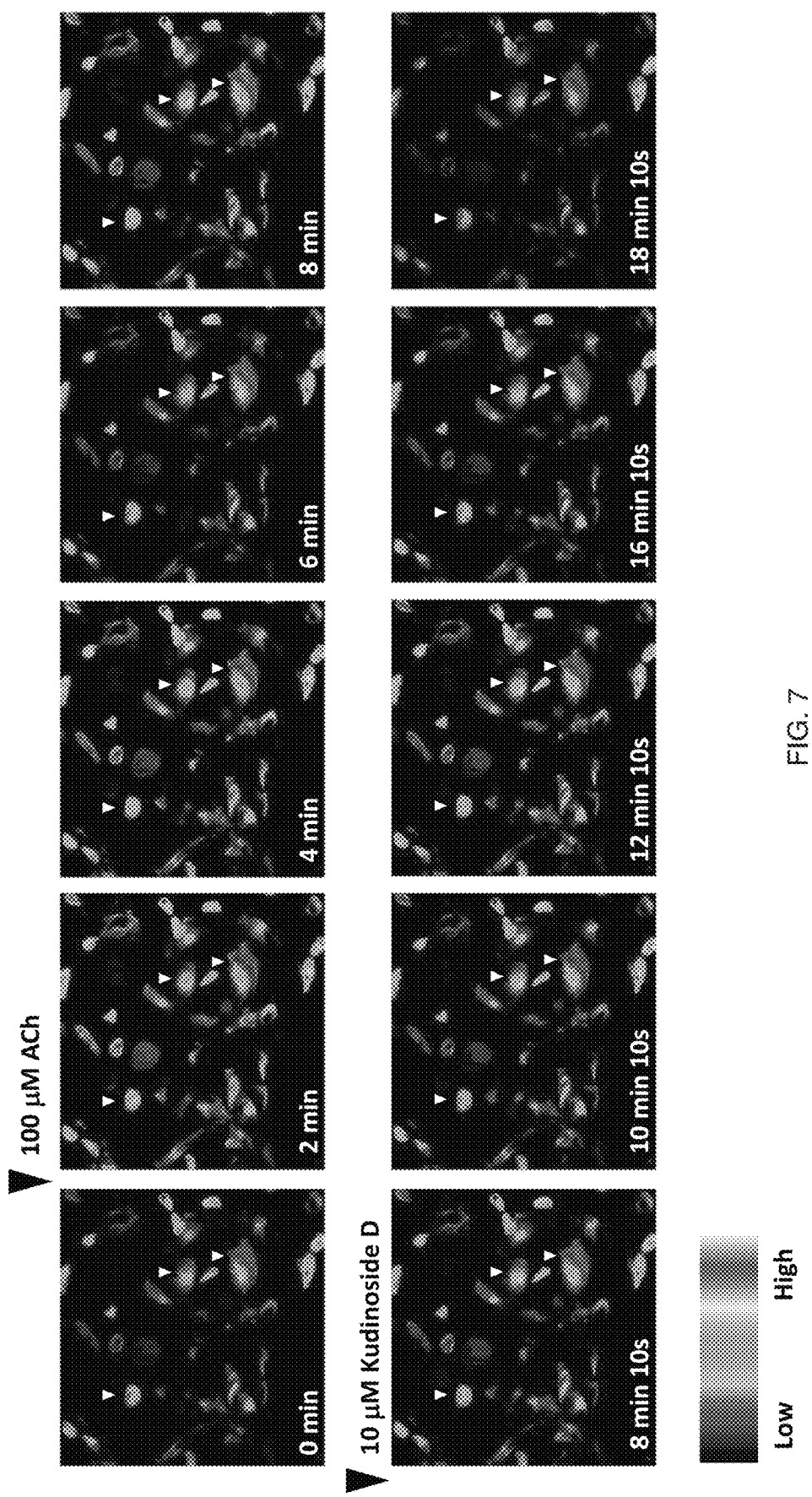
FIG. 7 shows that Kudinoside D causes decrease in cytosolic calcium. Primary airway smooth muscle cells were stimulated with 100 µM acetylcholine (ACh) (upper panels), resulting elevation and maintenance of calcium signals (arrow heads indicate typical alteration of the cells) for 8 minutes. After washing out ACh, new buffer containing 10 µM Kudinoside D was added, and then stimulated with 100 µM acetylcholine. A significant reduction of calcium could be observed around 16 to 18 minutes.

At rest condition, the smooth muscle cells showed weak but constant calcium signals. Upon addition of acetylcholine, the calcium signal became strong with a robust followed by declining to basal level, and smooth muscle contraction could be also detected during this process (FIG. 7). After pretreatment with kudinoside, however, the smooth muscle showed neither elevation of calcium signal nor cellular contraction (FIG. 7). These results indicate that kudinosides may reduce calcium influx during smooth muscle relaxation.

If the reduction of cytosolic calcium underlies the relaxation effect of kudinoside, fixation for cytosolic calcium concentration expectedly abolished the relaxation. When the muscle strip was skinned, pCa 4.5 elicited a sustained contraction. Treatment with kudinoside D could not relax this sustained contraction, and contrarily slightly enhanced it. These results shows that Kudinoside D did not relax smooth muscle at constant concentration of calcium. These results also indicate that modulation of calcium influx is required for the relaxation by kudinosides, and the mechanism underlying relaxation of kudinosides is involved modulation of calcium influx.

Figure 9B:
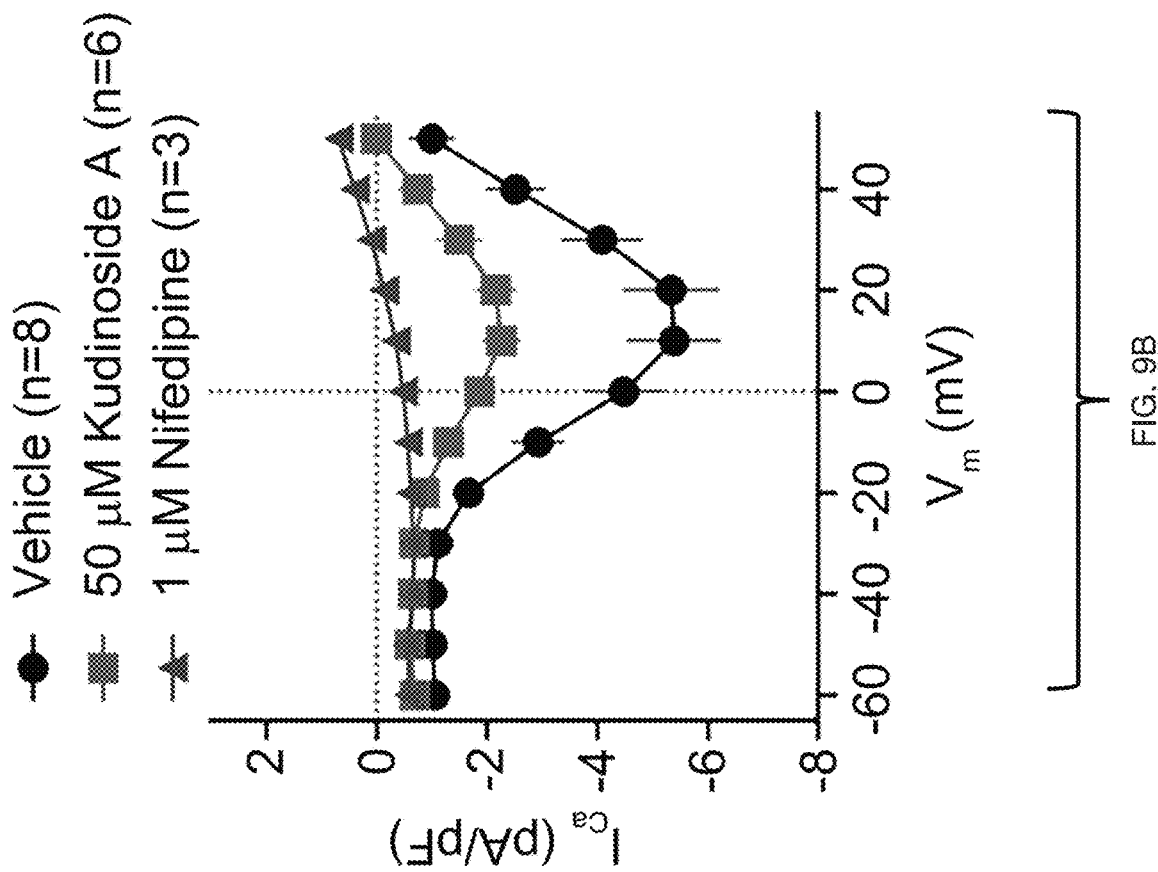
FIGS. 9A-B illustrate that L-type calcium channel may be a target of Kudinoside A. Whole-cell patch clamp recording of VDCC currents were performed under vehicle, or 50 µM Kudinoside A or 1 µM Nifedipine treatment.
Figure 9A:
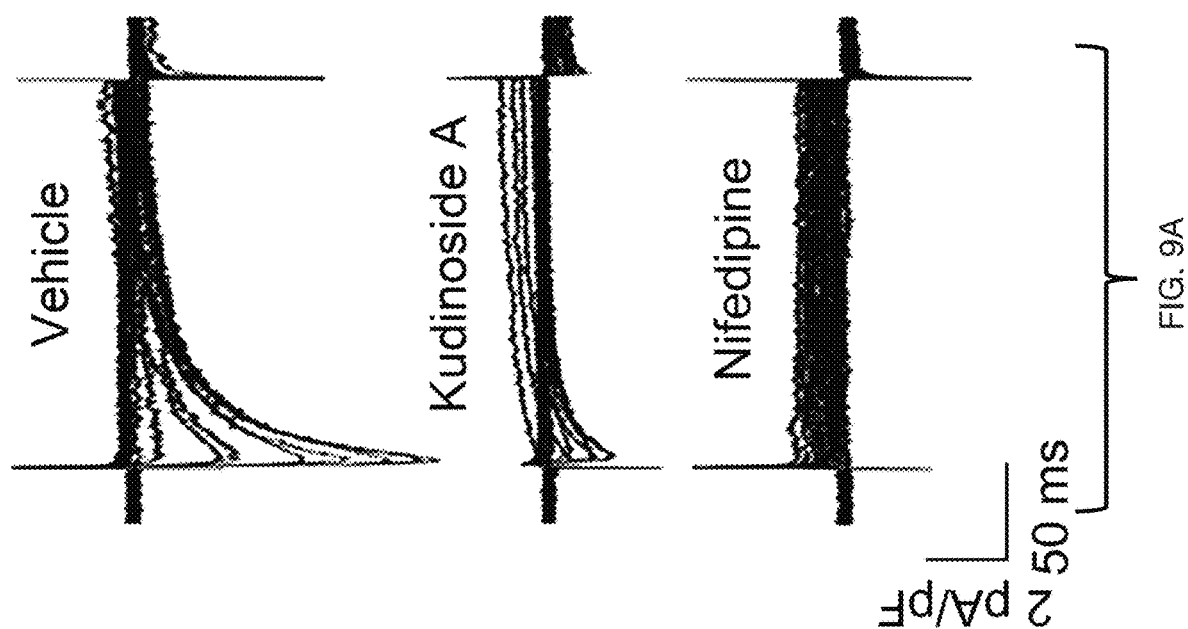

The augmented $Ca^{2+}$ in smooth muscle cells may be a second messenger for contraction initiating by both electromechanical coupling and pharmocomechanical coupling. And in these two general kinds of excitation, L-type calcium channel plays a role in generating the influx of $Ca^{2+}$ during contraction. So to identify the target of certain kudinosides, patch-clamp studies were used to examine the modulation of L-type calcium channel currents after Kudinosides treatment. In patch-clamp studies, whole-cell patch clamp recording of VDCC currents were performed at room temperature, in response to voltage pulses (−60 to +50 mV from a holding potential of −80 mV, 200 ms). 50 µM of Kudinoside A can decrease about 60% of the current generated by L-type calcium channel compared to the vehicle (FIGS. 9A-B). This results indicate that L-type calcium channel may be an essential target of certain kudinosides. However, as a positive control, 1 µM of Nifedipine, a well-established antagonist of L-type calcium channel, can almost eliminate the current of L-type calcium channel (FIGS. 9A-B). There may be more other targets of Kudinosides remaining to be determined.

Example 7

Outcome of *kudingcha* Extract in Human Asthma

Volunteer 20 to 50 years of age were eligible for enrollment if they had moderate asthma, diagnosed according to the guidelines of the Global Initiative for Asthma (See Table 3). All the patients require therapy with inhaled corticosteroids and beclomethasone or long-acting $beta_2$-adrenergic agonists or salmeterol or the equivalent to maintain reasonable control during asthma episode.

10 subjects who had been treated with inhaled therapy were randomly assigned. Because the volunteers with asthma symptoms are moderate and reversible or partial reversible, the individual person before treatment was designed as a control. The primary outcome was the acute release of dyspnea.

TABLE 3

Demographic and Clinical characteristics of subjects completing 2 weeks treatment

| Characteristic | | Note |
| --- | --- | --- |
| No. of subjects | 10 | 8 male/2 female |
| Age-yr | 26-51 | |
| Asthma severity | moderate 6/mild 4 | |
| Seasonal allergies present | 10 | |

TABLE 4

Acute outcome of subjects receiving once treatment

| | | after treatment | |
| --- | --- | --- | --- |
| Event | before treatment | 5 minute | 30 minutes |
| Dyspnea | 10 | 0 | 0 |
| Wheezing | 3 | 0 | 0 |
| Cough | 8 | | 3 |
| Chest discomfort | 5 | 3 | 3 |
| Nasal congestion | 3 | 3 | 3 |

Ten volunteers are from West-North and South of China where show a significant geological difference in seasons, culture and living styles. All the patients received 1-2 sprays of KE (55 mg/mL) treatment during asthma episode. Dyspnea and wheezing symptoms were significantly attenuated within 5 minutes, and no recurrence was observed within 30 minutes (Table 4). In most cases (8/10), the volunteers did not need second round of spray treatment within 12 hours. KE treatment also attenuated cough frequency after once spraying, but no inhibition of screatant production in airway and nose was observed (p>0.05). An interesting outcome is that the bronchitis may be inhibited significantly in 4/10 volunteers after repeated treatment with KE. During the treatment periods, there is no any side-effect in terms of breath, vomiting, allergy, dry mouth as well as other feeling. These results show that KE extract displays significant efficacy on release dyspnea of asthma, showing an acute complete response.

In order to test the effect of single substance in KE extract on asthma therapy, two volunteers (male 51 y; female 72 y) with severe asthma syndromes were treated with kudinoside A (20 mM) with an atomization device. After inhalation for 15 seconds, the male showed release of dyspnea at 5 minutes, and PEF value increased from 100 to 320. The release was maintained overnight. As a control of albuterol, this male volunteer showed release of dyspnea within 3 minutes, but the release could not be maintained overnight, and once more inhalation was required. For the female volunteer, similar result was obtained. This result shows that as one of active components of KE, kudinoside A also displays significant efficacy on release dyspnea of asthma.

What is claimed is:

1. A method for treating a pulmonary disease comprising administering to a subject in need thereof a therapeutically effective amount of an active ingredient consisting of a compound of formula (I) or stereoisomer, enantiomer, tautomer or a pharmaceutically acceptable salt thereof:

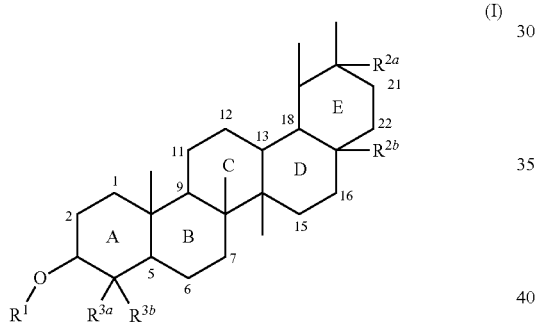

(I)

wherein:
the A, B, C, D, or E ring is independently fully saturated or partially saturated;
$R^1$ is a carbohydrate residue;
the positions of C2, C11, C12, and C19 are each independently substituted with hydrogen or —OH;
$R^{2a}$ and $R^{2b}$ together form —$CO_2$—;
$R^{3a}$ and $R^{3b}$ together form $CH_2$, or are each independently selected from —$CH_3$ or —$CH_2$—OH.

2. The method of claim 1, wherein the pulmonary disease includes at least one of asthma, chronic obstructive pulmonary disease, bronchitis, chronic or acute bronchoconstriction, adult respiratory distress syndrome, acute lung injury, and bronchiectasis.

3. The method of claim 1, wherein the carbohydrate residue is a monosaccharide residue or an oligosaccharide residue.

4. The method of claim 3, wherein:
the monosaccharide residue is selected from the group consisting of arabinose, glucuronic acid, 2-deoxy-glucuronic acid, glucose, and rhamnose; and/or
the oligosaccharide residue is a disaccharide residue, a trisaccharide residue, or a tetrasaccharide residue comprising any combination of glucose, arabinose, rhamnose and glucuronic acid.

5. The method of claim 1, wherein:
the A, B, C, and E rings are fully saturated; the D ring is partially saturated; the positions of C12 and C19 are each independently substituted with —OH; $R^{3a}$ and $R^{3b}$ are each independently —$CH_3$; and $R^1$ is a monosaccharide residue or an oligosaccharide residue; or
the A, B, C, and E rings are fully saturated; the D ring is partially saturated; the positions of C11 and C19 are each independently substituted with —OH; $R^{3a}$ and $R^{3b}$ are each independently —$CH_3$; and $R^1$ is a monosaccharide residue or an oligosaccharide residue; or
the A, B, and E rings are fully saturated; the C and D rings are partially saturated; the position of C19 is substituted with —OH; $R^{3a}$ and $R^{3b}$ are each independently —$CH_3$; and $R^1$ is a monosaccharide residue or an oligosaccharide residue;
or the compound of formula (I) is selected from:

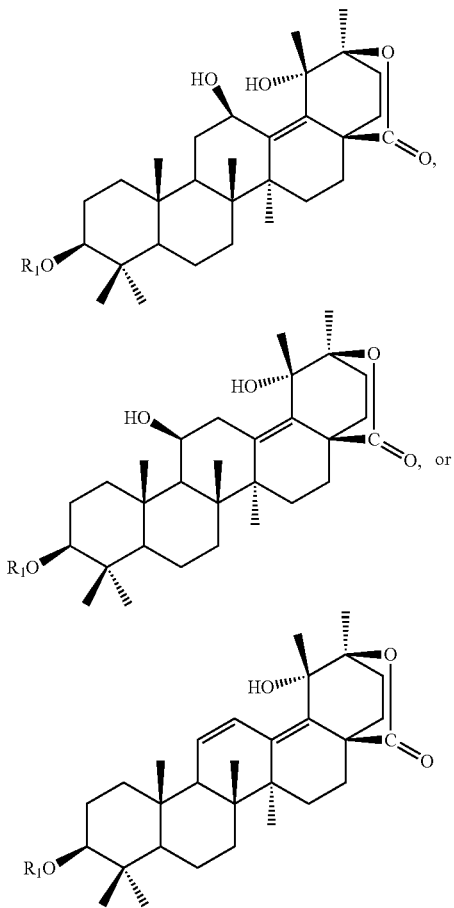

wherein $R^1$ is a monosaccharide residue or an oligosaccharide residue.

6. The method of claim 5, wherein:
the monosaccharide residue is selected from the group consisting of arabinose, glucuronic acid, 2-deoxy-glucuronic acid, glucose, and rhamnose; and/or
the oligosaccharide residue is a disaccharide residue, a trisaccharide residue, or a tetrasaccharide residue comprising any combination of glucose, arabinose, rhamnose and glucuronic acid.

7. The method of claim 1, wherein the compound of formula (I) is selected from the group consisting of kudinoside A, kudinoside B, kudinoside C, kudinoside D, kudinoside E, kudinoside F, kudinoside I, kudinoside J, Ilekudinoside H, Ilekudinoside I, and Ilekudinoside J.

8. The method of claim 1, wherein the compound of formula (I) is isolated from an extract of *kudingcha*.

9. The method of claim 1, wherein the subject is a human being or domestic animal.

10. The method of claim 1, wherein the administering comprises delivering the compound of formula (I) or stereoisomer, enantiomer, tautomer or a pharmaceutically acceptable salt thereof to the airway of the subject via inhalation.

11. The method of claim 1, wherein the compound of formula (I) or stereoisomer, enantiomer, tautomer or a pharmaceutically acceptable salt thereof is in a pharmaceutically acceptable carrier or in a delivery device.

12. The method of claim 1, wherein the compound of formula (I) or stereoisomer, enantiomer, tautomer or a pharmaceutically acceptable salt thereof forms an inhalation dosage form.

13. The method of claim 1, wherein the compound of formula (I) or stereoisomer, enantiomer, tautomer or a pharmaceutically acceptable salt thereof forms an aerosol form.

14. The method of claim 11, wherein the delivery device is a spray device or a pressurized delivery device.

* * * * *